(12) United States Patent
Marcussen et al.

(10) Patent No.: US 12,201,130 B2
(45) Date of Patent: Jan. 21, 2025

(54) STABLE GRANULES FOR FEED COMPOSITIONS

(71) Applicant: Novozymes A/S, Bagsvaerd (DK)

(72) Inventors: Erik Schmidt Marcussen, Ballerup (DK); Flemming Borup, Tygelsjoe (DK)

(73) Assignee: Novozymes A/S, Bagsverd (DK)

( * ) Notice: Subject to any disclaimer, the term of this patent is extended or adjusted under 35 U.S.C. 154(b) by 834 days.

(21) Appl. No.: 17/275,354

(22) PCT Filed: Sep. 11, 2019

(86) PCT No.: PCT/EP2019/074152
§ 371 (c)(1),
(2) Date: Mar. 11, 2021

(87) PCT Pub. No.: WO2020/053238
PCT Pub. Date: Mar. 19, 2020

(65) Prior Publication Data
US 2022/0046955 A1    Feb. 17, 2022

(30) Foreign Application Priority Data
Sep. 11, 2018 (EP) .................... 18193639

(51) Int. Cl.
| | | |
|---|---|---|
| *A23K 20/189* | (2016.01) | |
| *A23K 20/158* | (2016.01) | |
| *A23K 20/22* | (2016.01) | |
| *A23K 20/24* | (2016.01) | |
| *A23K 40/00* | (2016.01) | |
| *A23K 40/10* | (2016.01) | |
| *C12N 9/24* | (2006.01) | |
| *C12N 9/36* | (2006.01) | |
| *C12N 9/98* | (2006.01) | |

(52) U.S. Cl.
CPC .......... *A23K 20/189* (2016.05); *A23K 20/158* (2016.05); *A23K 20/22* (2016.05); *A23K 20/24* (2016.05); *A23K 40/00* (2016.05); *C12N 9/2462* (2013.01); *C12N 9/98* (2013.01); *C12Y 302/01017* (2013.01)

(58) Field of Classification Search
None
See application file for complete search history.

(56) References Cited

U.S. PATENT DOCUMENTS

| | | |
|---|---|---|
| 7,425,528 B2 | 9/2008 | Simonsen et al. |
| 9,663,775 B2 | 5/2017 | Schnorr |
| 2004/0033927 A1 | 2/2004 | Simonsen et al. |
| 2006/0073193 A1 | 4/2006 | Marcussen et al. |
| 2009/0263543 A1 | 10/2009 | Lohscheidt et al. |
| 2011/0097448 A1 | 4/2011 | Wong et al. |
| 2016/0030528 A1 | 2/2016 | Metcalf et al. |
| 2016/0237466 A1 | 8/2016 | Landowski et al. |

FOREIGN PATENT DOCUMENTS

| | | |
|---|---|---|
| CN | 101291594 A | 10/2008 |
| CN | 103957929 A | 7/2014 |
| CN | 104427878 A | 3/2015 |
| CN | 109475130 A | 3/2019 |
| EP | 3072399 A1 | 8/2007 |
| JP | 2015506667 A | 3/2015 |
| WO | 9212645 A1 | 8/1992 |
| WO | 0170240 A1 | 9/2001 |
| WO | 2006034710 A1 | 4/2006 |
| WO | 2013076253 A1 | 5/2013 |
| WO | 2013119468 A2 | 8/2013 |
| WO | 2014006090 A1 | 1/2014 |
| WO | 2018007153 A1 | 1/2018 |
| WO | 2018010966 A1 | 1/2018 |
| WO | 2018113743 A1 | 6/2018 |
| WO | 2018113745 A1 | 6/2018 |

OTHER PUBLICATIONS

Zou et al., Livestock and poultry industry, 2007, 2-3, 219.

*Primary Examiner* — Michelle F. Paguio Frising
(74) *Attorney, Agent, or Firm* — Adam Rucker

(57) ABSTRACT

The present invention relates to pelletized feed compositions comprising granules which comprise an inner salt layer and an outer hydrophobic layer. The invention further relates to the use of salt and hydrophobic coated granules for steam treated pelletized feed compositions.

20 Claims, No Drawings

Specification includes a Sequence Listing.

SEQUENCE LISTING

```
<160> NUMBER OF SEQ ID NOS: 4

<210> SEQ ID NO 1
<211> LENGTH: 838
<212> TYPE: DNA
<213> ORGANISM: Acremonium alcalophilum
<220> FEATURE:
<221> NAME/KEY: CDS
<222> LOCATION: (1)..(147)
<220> FEATURE:
<221> NAME/KEY: sig_peptide
<222> LOCATION: (1)..(57)
<220> FEATURE:
<221> NAME/KEY: CDS
<222> LOCATION: (302)..(835)

<400> SEQUENCE: 1 atg aag ctt ctt ccc tcc ttg att ggc ctg gcc agt ctg gcg tcc ctc     48
Met Lys Leu Leu Pro Ser Leu Ile Gly Leu Ala Ser Leu Ala Ser Leu
1               5                   10                  15 gcc gtc gcc cgg atc ccc ggc ttt gac att tcg ggc tgg caa ccg acc     96
Ala Val Ala Arg Ile Pro Gly Phe Asp Ile Ser Gly Trp Gln Pro Thr
            20                  25                  30
```

| | | |
|---|---|---|
| acc gac ttt gca agg gcg tat gct aat gga gat cgt ttc gtc tac atc<br>Thr Asp Phe Ala Arg Ala Tyr Ala Asn Gly Asp Arg Phe Val Tyr Ile<br>35                          40                          45 | | 144 |
| aag gtacgttcaa ccttgccacc aagttgcgaa cccgagacaa gactgtgacc<br>Lys | | 197 |
| gcctcctttg ccctggggca gctcacgcac ccagcagcat cccatccccc ggccccccac | | 257 |
| gtaccaccgg aaagctaaca tcaacccccct accactgcta ccag gcc acc gag ggc<br>                                                                                                                                        Ala Thr Glu Gly<br>                                                                                                                                        50 | | 313 |
| acc aca ttc aag agc tcc gca ttc agc cgc cag tac acc ggc gca acg<br>Thr Thr Phe Lys Ser Ser Ala Phe Ser Arg Gln Tyr Thr Gly Ala Thr<br>        55                         60                          65 | | 361 |
| caa aac ggc ttc atc cgc ggc gcc tac cac ttc gcc cag ccc gcc gcg<br>Gln Asn Gly Phe Ile Arg Gly Ala Tyr His Phe Ala Gln Pro Ala Ala<br>70                          75                          80                          85 | | 409 |
| tcc tcg ggc gcc gcg cag gcg aga tac ttc gcc agc aac ggc ggc ggc<br>Ser Ser Gly Ala Ala Gln Ala Arg Tyr Phe Ala Ser Asn Gly Gly Gly<br>                90                          95                          100 | | 457 |
| tgg tcc aag gac ggc atc acc ctg ccc ggg gcg ctg gac atc gag tac<br>Trp Ser Lys Asp Gly Ile Thr Leu Pro Gly Ala Leu Asp Ile Glu Tyr<br>                      105                        110                        115 | | 505 |
| aac ccc aac ggc gcc acc tgc tac ggc ctc tcg caa tcg gcc atg gtg<br>Asn Pro Asn Gly Ala Thr Cys Tyr Gly Leu Ser Gln Ser Ala Met Val<br>                      120                        125                        130 | | 553 |
| aac tgg atc gag gac ttt gtc acc acc tac cac ggc atc acc tcc cgc<br>Asn Trp Ile Glu Asp Phe Val Thr Thr Tyr His Gly Ile Thr Ser Arg<br>135                        140                        145 | | 601 |
| tgg ccc gtc atc tac acc acc acc gac tgg tgg acc cag tgc acc ggc<br>Trp Pro Val Ile Tyr Thr Thr Thr Asp Trp Trp Thr Gln Cys Thr Gly<br>150                        155                        160                        165 | | 649 |
| aac tcc aac cgc ttc gcg aac cgc tgc ccg ctg tgg atc gcc cgc tac<br>Asn Ser Asn Arg Phe Ala Asn Arg Cys Pro Leu Trp Ile Ala Arg Tyr<br>                      170                        175                        180 | | 697 |
| gcc agc tcc gtc ggc act ctg ccc aat ggc tgg ggc ttt tac acc ttc<br>Ala Ser Ser Val Gly Thr Leu Pro Asn Gly Trp Gly Phe Tyr Thr Phe<br>                    185                        190                        195 | | 745 |
| tgg cag tac aac gac aag tat cct cag ggc ggt gat tcg aac tgg ttc<br>Trp Gln Tyr Asn Asp Lys Tyr Pro Gln Gly Gly Asp Ser Asn Trp Phe<br>200                        205                        210 | | 793 |
| aac ggc gat gcg tcg cgt ctc agg gct ctc gct aac gga gac taa<br>Asn Gly Asp Ala Ser Arg Leu Arg Ala Leu Ala Asn Gly Asp<br>        215                        220                        225 | | 838 |

<210> SEQ ID NO 2
<211> LENGTH: 227
<212> TYPE: PRT
<213> ORGANISM: Acremonium alcalophilum

<400> SEQUENCE: 2

Met Lys Leu Leu Pro Ser Leu Ile Gly Leu Ala Ser Leu Ala Ser Leu
1                  5                        10                        15

Ala Val Ala Arg Ile Pro Gly Phe Asp Ile Ser Gly Trp Gln Pro Thr
                  20                        25                        30

Thr Asp Phe Ala Arg Ala Tyr Ala Asn Gly Asp Arg Phe Val Tyr Ile
                  35                        40                        45

Lys Ala Thr Glu Gly Thr Thr Phe Lys Ser Ser Ala Phe Ser Arg Gln
        50                        55                        60

Tyr Thr Gly Ala Thr Gln Asn Gly Phe Ile Arg Gly Ala Tyr His Phe
65                  70                        75                        80

-continued

```
Ala Gln Pro Ala Ala Ser Ser Gly Ala Ala Gln Ala Arg Tyr Phe Ala
                 85                  90                  95

Ser Asn Gly Gly Gly Trp Ser Lys Asp Gly Ile Thr Leu Pro Gly Ala
            100                 105                 110

Leu Asp Ile Glu Tyr Asn Pro Asn Gly Ala Thr Cys Tyr Gly Leu Ser
        115                 120                 125

Gln Ser Ala Met Val Asn Trp Ile Glu Asp Phe Val Thr Thr Tyr His
    130                 135                 140

Gly Ile Thr Ser Arg Trp Pro Val Ile Tyr Thr Thr Thr Asp Trp Trp
145                 150                 155                 160

Thr Gln Cys Thr Gly Asn Ser Asn Arg Phe Ala Asn Arg Cys Pro Leu
                165                 170                 175

Trp Ile Ala Arg Tyr Ala Ser Ser Val Gly Thr Leu Pro Asn Gly Trp
            180                 185                 190

Gly Phe Tyr Thr Phe Trp Gln Tyr Asn Asp Lys Tyr Pro Gln Gly Gly
        195                 200                 205

Asp Ser Asn Trp Phe Asn Gly Asp Ala Ser Arg Leu Arg Ala Leu Ala
    210                 215                 220

Asn Gly Asp
225
```

<210> SEQ ID NO 3
<211> LENGTH: 747
<212> TYPE: DNA
<213> ORGANISM: Artificial Sequence
<220> FEATURE:
<223> OTHER INFORMATION: Synthetic construct
<220> FEATURE:
<221> NAME/KEY: CDS
<222> LOCATION: (1)..(744)
<220> FEATURE:
<221> NAME/KEY: sig_peptide
<222> LOCATION: (1)..(69)
<220> FEATURE:
<221> NAME/KEY: mat_peptide
<222> LOCATION: (121)..(744)

<400> SEQUENCE: 3

```
atg aag ttc ttc acc acc atc ctc agc acc gcc agc ctt gtt gct gct      48
Met Lys Phe Phe Thr Thr Ile Leu Ser Thr Ala Ser Leu Val Ala Ala
-40             -35                 -30                 -25 ctc ccc gcc gct gtt gac tcg aac cat acc ccg gcc gct cct gaa ctt      96
Leu Pro Ala Ala Val Asp Ser Asn His Thr Pro Ala Ala Pro Glu Leu
            -20                 -15                 -10 gtt gcc cgg agt cct att cgt cga cgc att ccc gga ttc gat atc tcg    144
Val Ala Arg Ser Pro Ile Arg Arg Arg Ile Pro Gly Phe Asp Ile Ser
        -5                  -1  1               5 gga tgg cag ccg acg acg gac ttc gca agg gcg tac gca aac gga gac    192
Gly Trp Gln Pro Thr Thr Asp Phe Ala Arg Ala Tyr Ala Asn Gly Asp
10                  15                  20 cga ttc gtg tac atc aag gca aca gag gga aca aca ttc aaa tcg tcg    240
Arg Phe Val Tyr Ile Lys Ala Thr Glu Gly Thr Thr Phe Lys Ser Ser
25                  30                  35                  40 gca ttc tcc agg cag tac acc gga gca acc cag aac ggc ttc atc cga    288
Ala Phe Ser Arg Gln Tyr Thr Gly Ala Thr Gln Asn Gly Phe Ile Arg
                45                  50                  55 gga gcc tac cac ttc gcc cag cct gca gcc tcc tcg gga gca gcc cag    336
Gly Ala Tyr His Phe Ala Gln Pro Ala Ala Ser Ser Gly Ala Ala Gln
            60                  65                  70 gca agg tac ttc gca tcg aac ggt ggc ggt tgg tcc aag gac ggt atc    384
Ala Arg Tyr Phe Ala Ser Asn Gly Gly Gly Trp Ser Lys Asp Gly Ile
```

```
Ala Arg Tyr Phe Ala Ser Asn Gly Gly Gly Trp Ser Lys Asp Gly Ile
        75                  80                  85 acc ctc cct ggt gcc ttg gat atc gag tac aac ccc aac gga gca aca      432
Thr Leu Pro Gly Ala Leu Asp Ile Glu Tyr Asn Pro Asn Gly Ala Thr
        90                  95                 100 tgt tat ggt ctc tcg cag tcg gcg atg gtg aac tgg att gag gac ttc      480
Cys Tyr Gly Leu Ser Gln Ser Ala Met Val Asn Trp Ile Glu Asp Phe
105                 110                 115                 120 gtg aca acc tac cac ggc atc acc tcg agg tgg cct gtg atc tac acc      528
Val Thr Thr Tyr His Gly Ile Thr Ser Arg Trp Pro Val Ile Tyr Thr
                    125                 130                 135 aca acc gac tgg tgg acg cag tgt acc ggc aac tcc aac cga ttc gcg      576
Thr Thr Asp Trp Trp Thr Gln Cys Thr Gly Asn Ser Asn Arg Phe Ala
            140                 145                 150 aac agg tgt ccg ctc tgg atc gcg agg tat gcc tcc tcc gtc ggc acc      624
Asn Arg Cys Pro Leu Trp Ile Ala Arg Tyr Ala Ser Ser Val Gly Thr
        155                 160                 165 ctc ccg aac gga tgg ggc ttc tat acc ttc tgg cag tac aac gat aag      672
Leu Pro Asn Gly Trp Gly Phe Tyr Thr Phe Trp Gln Tyr Asn Asp Lys
170                 175                 180 tac ccc cag gga gga gat tcc aac tgg ttc aac ggt gat gca tcg agg      720
Tyr Pro Gln Gly Gly Asp Ser Asn Trp Phe Asn Gly Asp Ala Ser Arg
185                 190                 195                 200 ctc agg gca ttg gcg aac ggc gat tag                                  747
Leu Arg Ala Leu Ala Asn Gly Asp
                205

<210> SEQ ID NO 4
<211> LENGTH: 248
<212> TYPE: PRT
<213> ORGANISM: Artificial Sequence
<220> FEATURE:
<223> OTHER INFORMATION: Synthetic Construct

<400> SEQUENCE: 4

Met Lys Phe Phe Thr Thr Ile Leu Ser Thr Ala Ser Leu Val Ala Ala
-40                 -35                 -30                 -25

Leu Pro Ala Ala Val Asp Ser Asn His Thr Pro Ala Ala Pro Glu Leu
                -20                 -15                 -10

Val Ala Arg Ser Pro Ile Arg Arg Ile Pro Gly Phe Asp Ile Ser
            -5                  -1   1                   5

Gly Trp Gln Pro Thr Thr Asp Phe Ala Arg Ala Tyr Ala Asn Gly Asp
        10                  15                  20

Arg Phe Val Tyr Ile Lys Ala Thr Glu Gly Thr Thr Phe Lys Ser Ser
25                  30                  35                  40

Ala Phe Ser Arg Gln Tyr Thr Gly Ala Thr Gln Asn Gly Phe Ile Arg
                45                  50                  55

Gly Ala Tyr His Phe Ala Gln Pro Ala Ala Ser Ser Gly Ala Ala Gln
            60                  65                  70

Ala Arg Tyr Phe Ala Ser Asn Gly Gly Gly Trp Ser Lys Asp Gly Ile
        75                  80                  85

Thr Leu Pro Gly Ala Leu Asp Ile Glu Tyr Asn Pro Asn Gly Ala Thr
        90                  95                 100

Cys Tyr Gly Leu Ser Gln Ser Ala Met Val Asn Trp Ile Glu Asp Phe
105                 110                 115                 120

Val Thr Thr Tyr His Gly Ile Thr Ser Arg Trp Pro Val Ile Tyr Thr
                    125                 130                 135

Thr Thr Asp Trp Trp Thr Gln Cys Thr Gly Asn Ser Asn Arg Phe Ala
```

-continued

```
                    140                 145                 150
Asn Arg Cys Pro Leu Trp Ile Ala Arg Tyr Ala Ser Ser Val Gly Thr
        155                 160                 165

Leu Pro Asn Gly Trp Gly Phe Tyr Thr Phe Trp Gln Tyr Asn Asp Lys
    170                 175                 180

Tyr Pro Gln Gly Gly Asp Ser Asn Trp Phe Asn Gly Asp Ala Ser Arg
185                 190                 195                 200

Leu Arg Ala Leu Ala Asn Gly Asp
                205
```

STABLE GRANULES FOR FEED COMPOSITIONS

CROSS-REFERENCE TO RELATED APPLICATIONS

This application is a 35 U.S.C. 371 national application of international application no. PCT/EP2019/074152 filed Sep. 11, 2019, which claims priority or the benefit under 35 U.S.C. 119 of European application no. 18193639.4 filed Sep. 11, 2018, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to pelletized feed compositions comprising granules which comprise an inner salt layer and an outer hydrophobic layer. The invention further relates to the use of salt and hydrophobic coated granules for steam treated pelletized feed compositions.

BACKGROUND OF THE INVENTION

Animal feed is typically provided as pellets containing the ingredients desired for the animals. This has the advantage that all ingredients needed by the animal are available, the digestibility of especially the starch fraction of the feed is increased and dust from the ingredients is reduced.

During production of feed pellets, the pellets are stream treated at elevated temperature with the purpose of killing bacteria from e.g. *Salmonella*. Often, active compounds such as enzymes present in the feed pellets are not stable at elevated temperature and under high humidity, and thus, a large surplus of enzymes in feed pellets, is needed. Alternatively, application of an enzyme coating onto enzyme free feed pellets may be used; however, this coating process is cumbersome and is often not compatible with existing feed plants.

A method of improving stability of the active compound is to provide granules comprising the active compound in the core and a suitable coating agent coated on the core before steam treatment and pelletization. WO 92/12645 describes T-granules which are coated with a fat or a wax, and feed components which are steam treated and subsequently pelletized. WO 2006/034710 discloses enzyme containing granules which are coated with a salt coating before pelletization.

There is however still a need for further improving the stability of active compounds such as enzymes in pelletized feed products.

SUMMARY OF THE INVENTION

The invention provides a pelletized feed composition comprising a granule comprising a core and a coating, wherein the core comprises a muramidase and the coating comprises an inner salt layer and an outer hydrophobic layer.

The invention further provides a granule comprising a core and a coating, wherein the core comprises a muramidase and the coating comprises an inner salt layer and an outer hydrophobic layer.

In a further embodiment is provided a granule comprising a core and a coating, wherein the core comprises a muramidase and the coating comprises an inner salt layer and an outer hydrophobic layer, wherein the granule comprises at least 75% of muramidase with retained activity after steam pelleting compared to the activity before steam pelleting, and wherein the granule further comprises one or more of the following:
  i. the particle size of the granule is below 1200 µm,
  ii. the thickness of the inner inner salt layer is at least 15 µm,
  iii. the thickness of the outer hydrophobic coating is at least 1 µm, and
  iv. the muramidase is thermo labile.

Also provided by the invention is a method for feeding animals, a method for manufacturing a feed composition, a method for improving the stability of muramidase and a method for improving the stability of muramidase in a mash composition having a humidity above 12%.

A yet further embodiment provides for the use of a granule comprising a core comprising a muramidase, an inner salt layer and an outer hydrophobic layer for preparing steam treated pelletized feed compositions.

Overview of Sequence Listing

SEQ ID NO: 1 is the DNA sequence of the P242M9 GH25 gene as isolated from *Acremonium alkalophilum* CBS114.92.

SEQ ID NO: 2 is the amino acid sequence as deduced from SEQ ID NO: 1.

SEQ ID NO: 3 is the DNA sequence of a synthetically optimised GH25 gene.

SEQ ID NO: 4 is the amino acid sequence as deduced from SEQ ID NO: 3.

DETAILED DESCRIPTION OF THE INVENTION

Definitions

Constant humidity: The term "constant humidity" (in the context of the invention sometimes abbreviated as "CH") of a compound or substance is to be understood as the % RH of atmospheric air in equilibrium with a saturated aqueous solution of said compound in contact with the solid phase of said compound, all confined within a closed space at a given temperature. This definition is in accordance with "*Handbook of chemistry and physics*" CRC Press, Inc., Cleveland, USA, 58th edition, p E46, 1977-1978. Accordingly $CH_{20° C.}$=50% for a compound means that air with a 50% humidity will be in equilibrium with a saturated aqueous solution of the compound at 20° C. Accordingly the term constant humidity is a measure of the hygroscopic properties of a compound.

Dust: The term "dust" in connection with granules or powders refers to the tendency of a granule or powder, upon handling, to liberate fine airborne particles. Granule or powder dust is routinely measured in the industry and may be measured by several different techniques. Well known methods for measuring enzyme dust e.g. include the Elutriation assay and the Heubach Type 1 assay. In the elutriation test, enzyme granules are placed on a glass frit within a tall glass tube, and fluidized with a constant dry air stream over a fixed time period. In the Heubach assay, granules are placed in a small, cylindrical steel chamber fitted with a rotating paddle and steel balls; the granules are pushed around by the paddle and balls, while a dry air stream percolates up through the chamber. In both tests, dust stripped from the particles by the air stream is captured on a glass fiber filter for subsequent weight measurement and activity determination. Additional details of these tests can be found, for example, in "Enzymes In Detergency," ed. Jan H. van Ee, et al., Chpt. 15, pgs. 310-312 (Marcel Dekker, Inc., New York, NY (1997)), and references cited therein.

GH25 muramidase: The term "GH25 muramidase" is used for muramidases belonging to the GH25 family. The GH25 family is a classification of enzymes according to the Henrissat glycosyl hydrolase family classification (Henrissat B., A classification of glycosyl hydrolases based on amino-acid sequence similarities. Biochem. J. 280:309-316 (1991); Henrissat B., Bairoch A. New families in the classification of glycosyl hydrolases based on amino-acid sequence similarities. Biochem. J. 293:781-788 (1993); Henrissat B., Bairoch A. Updating the sequence-based classification of glycosyl hydrolases. Biochem. J. 316:695-696 (1996); Davies G., Henrissat B. Structures and mechanisms of glycosyl hydrolases. Structure 3:853-859 (1995)). Besides GH25, other enzyme hydrolase families with lysozyme (EC 3.2.1.17) activity are GH22, GH23 and GH24.

Hydrogenated: The term "hydrogenated" is used for saturation of unsaturated carbohy-drate chains, e.g. in triglycerides, wherein carbon=carbon double bonds are converted to carbon-carbon single bonds.

Mash composition: Mash composition is the nutritionally complete composition of cereals, cereal products and optional supplements in a ground form e.g. comprising wheat, maize, . . . which has not been pelleted and conditioned.

Particle size: By particle size of the granule is meant the mass mean diameter of the granules.

Pelletized feed composition: The term "pelletized feed composition" is intended to mean the feed composition after pelleting and conditioning, i.e. the feed pellets to be fed to the animals.

% RH: The term "% RH" is to be understood as the relative humidity of air. 100% RH is air saturated with water moisture at a fixed temperature and % RH thus reflects the percent moisture saturation of the air.

Solution: A solution is defined as a homogeneous mixture of two or more substances.

Suspension: A suspension is defined as fine particles suspended in a fluid.

Introduction

Enzymes such as e.g. muramidase comprised in a feed product which has been pelleted from a mash composition having a humidity of e.g. 13-15% are prone to have a lower stability than in feed products from mash compositions with lower humidity. With the invention it has surprisingly been found that the stability of muramidase is increased in general when the muramidase is comprised in granules further comprising an inner salt layer and an outer hydrophobic layer. It was furthermore surprisingly found that with the invention, the stability of muramidase is also increased for muramidases which have been pelleted from mash compositions with a humidity above 11%, such as from 13% to 15% humidity. Thus, the stability of muramidase in feed which has been exposed to steam treatment is improved compared to the stability of steam treated muramidase which is not comprised in the granules of the invention. A further advantage of the invention is that the granules only release a low amount of dust and the shelf life of the granules is retained.

The Granule

When referring to the granule of the present invention it can either be a single granule or several granules.

The granule of the present invention is particularly well suited for steam pelleting and as part of a steam treated pelletized feed composition. The granule comprises a core and a coating, wherein the core comprises a muramidase and the coating comprises an inner salt layer and an outer hydrophobic layer.

Suitable particle sizes of the granule of the present invention is found to be 50-2000 μm, more particularly 100-1500 μm. In an embodiment of the invention, the particle size of the granule is more than 250 μm. In a further embodiment of the invention, the particle size is below 1200 μm. In yet a further embodiment, the particle size is between 250-1200 μm. In another embodiment of the present invention the particle size of the finished granule is 250-900 μm. In yet another embodiment of the present invention the mean particle size of the finished granule is 500-700 μm. In still another embodiment of the present invention the particle size of the finished granule is 600-1200 μm. In still another embodiment of the present invention, the particle size of the finished granule is 600-900 μm.

The Core

The core comprises a muramidase, such as a GH25 muramidase, in the form of concentrated dry matter.

The core can either be
1. a homogeneous blend of enzymes including one or more muramidases,
or
2. an inert particle with muramidase and optionally further enzymes applied onto it,
or
3. a homogenous blend of enzymes including one or more muramidases and materials which act as binders which are coated with one or more muramidases.

The core particle size of the present invention is in a particular embodiment 20-1900 μm. In a more particular embodiment of the present invention the core particle size is 50-1400 μm. In an even more particular embodiment of the present invention the core particle size is 150-1100 μm. In a most particular embodiment of the present invention the core particle size is 250-1200 μm. In the instances where the core comprises an inert particle, the inert particle may be water soluble or water insoluble, e.g. starch, e.g. in the form of cassava or wheat; or a sugar (such as sucrose or lactose), or a salt (such as sodium chloride or sodium sulphate). Suitable inert particle materials of the present invention include inorganic salts, sugars, sugar alcohols, small organic molecules such as organic acids or salts, minerals such as clays or silicates or a combination of two or more of these. Inert particles may be produced by a variety of granulation techniques including: crystallisation, precipitation, pan-coating, fluid bed coating, fluid bed agglomeration, rotary atomization, extrusion, prilling, spheronization, size reduction methods, drum granulation, and/or high shear granulation.

In the instances where the core comprises one or more binders, the binders may be synthetic polymers such as e.g. a vinyl polymer, polyvinyl pyrrolidone (PVP), polyvinyl alcohol (PVA), polyvinyl acetate, polyacrylate, polymethacrylate, poly-acrylamide, polysulfonate, polycarboxylate, and copolymers thereof, waxes including fats, fermentation broth, carbohydrates, salts or polypeptides. In a particular embodiment, the binder is a polypeptide. The polypeptide may be selected from gelatin, collagen, casein, chitosan, poly aspartic acid and poly glutamatic acid. In another particular embodiment the binder is a cellulose derivative such as hydroxypropyl cellulose, methyl cellulose or CMC. A suitable binder is a carbohydrate binder such as dextrin e.g Glucidex 21D or Avedex W80.

In one embodiment, the core may comprise a salt. The salt may be an inorganic salt, e.g. a salt of sulfate, sulfite, phosphate, phosphonate, nitrate, chloride or carbonate or salts of simple organic acids (less than 10 carbon atoms e.g. 6 or less carbon atoms) such as citrate, malonate or acetate. Examples of cations in these salt are alkali or earth alkali metal ions, although the ammonium ion or metal ions of the first transition series, such as sodium, potassium, magnesium, calcium, zinc or aluminium. Examples of anions include chloride, iodide, sulfate, sulfite, bisulfite, thiosulfate, phosphate, monobasic phosphate, dibasic phosphate, hypophosphite, dihydrogen pyrophosphate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used. Specific examples include $NaH_2PO_4$, $Na_2HPO_4$, $Na_3PO_4$, $(NH_4)H_2PO_4$, $K_2HPO_4$, $KH_2PO_4$, $Na_2SO_4$, $K_2SO_4$, $KHSO_4$, $ZnSO_4$, $MgSO_4$, $CuSO_4$, $Mg(NO_3)_2$, $(NH_4)_2SO_4$, sodium borate, magnesium acetate and sodium citrate. The salt in the core of the particle may also be a hydrated salt, i.e. a crystalline salt hydrate with bound water(s) of crystallization, such as described in WO 99/32595. Examples of hydrated salts include magnesium sulfate heptahydrate ($MgSO_4(7H_2O)$), zinc sulfate heptahydrate ($ZnSO_4(7H_2O)$), sodium phos-phate dibasic heptahydrate ($Na_2HPO_4(7H_2O)$), magnesium nitrate hexahydrate ($Mg(NO_3)_2(6H_2O)$), sodium borate decahydrate, sodium citrate dihydrate and magnesium ace-tate tetrahydrate.

In one embodiment, the core and/or the inner salt layer may comprise a moisture absorbing compound. The moisture absorbing compound serves as a buffer which is able to decrease water activity by reducing free water in contact with the muramidase in the granule. If the moisture absorbing compound is added to the core, it is important that there is excessive buffer capacity to remove the water present after application of the inner salt layer. In one embodiment, the moisture absorbing compound has a water uptake of more than 3%, such as more than 5%, such as more than 10% water uptake. The water uptake is found as the equilibrium water uptake at 25° C. and 70% relative humidity after one week. The amount of moisture absorbing compound added to the granule is more than 1%, more than 2%, more than 5%, or more than 10% w/w of the granule.

The moisture absorbing compound may be either organic or inorganic compounds and may be selected from, but is not limited to, the group consisting of flour, starch, corn cob products, cellulose and silica gel.

The granule may comprise additional materials such as process aids, fillers, fibre materials, stabilizing agents, solubilising agents, suspension agents, viscosity regulating agents, light spheres, plasticizers, salts, lubricants and fragrances. Process aids may e.g. be provided as powdering and may e.g. be $CaCO_3$, talcum and/or kaolin. Suitable fillers are water soluble and/or insoluble inorganic salts such as finely ground alkali sulphate, alkali carbonate and/or alkali chloride, clays such as kaolin (e.g. SPESWHITE™, English China Clay), bentonites, talcs, zeolites, chalk, calcium carbonate and/or silicates. Typical fillers are di-sodium sulphate and calcium-lignosulphonate. Stabilising or protective agents are such as conventionally used in the field of granulation. Stabilising or protective agents may fall into several categories: alkaline or neutral materials, reducing agents, antioxidants and/or salts of first transition series metal ions. Each of these may be used in conjunction with other protective agents of the same or different categories. Examples of alkaline protective agents are alkali metal silicates, carbonates or bicarbonates. Examples of reducing protective agents are salts of sulfite, thiosulfite, thiosulfate or $MnSO_4$ while examples of antioxidants are methionine, butylated hydroxytoluene (BHT) or butylated hydroxyanisol (BHA). In particular stabilising agents may be salts of thiosulfates, e.g. sodium thiosulfate or methionine. Still other examples of useful stabilizers are gelatine, urea, sorbitol, glycerol, casein, Poly vinyl pyrrolidone (PVP), hydroxypropylmethylcellulose (HPMC), carboxymethyl cellulose (CMC), hydroxyethylcellulose (HEC), powder of skimmed milk and/or edible oils, such as soy oil or canola oil. Particular stabilizing agents in feed granules are a lactic acid source or starch. A preferred lactic acid source is corn steep liquor. It is also well known in the art that enzyme substrates such as starch, lipids, proteins etc can act as stabilizers for enzymes.

Muramidase

A muramidase for use in the present invention may be any muramidase, a combination of two or more muramidases or a combination of any muramidase and one or more further enzymes. Accordingly, when reference is made to "a muramidase" this will in general be understood to include one muramidase, a combination of two or more muramidases or a combination of a muramidase and one or more further enzymes.

A muramidase is an O-glycosyl hydrolase, which has lysozyme activity and thus catalyses the hydrolysis of the glycosidic bond between two or more carbohydrates, or between a carbohydrate and a non-carbohydrate moiety. Muramidases cleave the glycosidic bond between certain residues in mucopolysaccharides and mucopeptides of bacterial cell walls, such as 1,4-beta-linkages between N-acetylmuramic acid and N-acetyl-D-glucosamine residues in a peptidoglycan and between N-acetyl-D-glucosamine residues in chitodextrins, resulting in bacteriolysis. Muramidase belongs to the enzyme class EC 3.2.1.17.

It is to be understood that muramidase variants (produced, for example, by recombinant techniques) are included within the meaning of the term "muramidase". Examples of such muramidase variants are disclosed, e.g. in WO 2013/076253, WO 2018/113743 and WO 2018/113745.

In one embodiment, the muramidase for use in the invention is a GH25 muramidase. In one embodiment, the muramidase for use in the invention has ability to lyse bacterial cell walls.

In one embodiment, the muramidase for use in the invention has improved lysozyme activity a) compared to the lysozyme activity of hen eggwhite lysozyme (HEWL) as determined by any one of i) Method for the Determination of Lysozyme Activity Against *Micrococcus lysodeikticus* as determined according to the turbidity assay described in example 4 of WO 2013/076253 and ii) Method for the Determination of Lysozyme Activity Against *Lactobacillus johnsonfi* as determined by Method for the Determination of Lysozyme Activity Against *Lactobacillus johnsonfi* as described in example 56 of WO 2018/113745. In one embodiment, the muramidase for use in the invention has lysozyme activity against the peptidoglycans found in the cell walls of *Micrococcus lysodeikticus* as determined according to the turbidity assay described in example 4 of WO 2013/076253. In one embodiment, the muramidase for use in the invention has lysozyme activity against *Lactobacillus johnsonfi* as determined by Method for the Determination of Lysozyme Activity Against *Lactobacillus johnsonfi* as described in example 56 of WO 2018/113745.

In one embodiment, the muramidase for use in the invention is an isolated polypeptide having lysozyme activity and is selected from the group consisting of:
  a. a polypeptide having at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2 or to the mature polypeptide of SEQ ID NO: 4;
  b. a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1 or to the mature polypeptide coding sequence of SEQ ID NO: 3;
  c. a polypeptide encoded by a polynucleotide that hybridizes under medium-high stringency conditions with the mature polypeptide coding sequence of SEQ ID NO: 1 or SEQ ID NO: 3, or the full-length complement thereof;
  d. a variant of the mature polypeptide of SEQ ID NO: 2 or SEQ ID NO: 4, comprising a substitution, deletion, and/or insertion at one or more (e.g., several) positions; and
  e. a fragment a fragment of the polypeptide of (a), (b), (c) or (d) that has lysozyme activity.

In one embodiment, the muramidase for use in the invention is selected among polypeptides comprising or consisting of the mature polypeptide of SEQ ID NO: 2 or SEQ ID NO: 4.

In one embodiment, the muramidase for use in the invention is an isolated polypeptide which is mentioned in WO 2018/113743 and is selected the group consisting of:
  (a) a polypeptide having at least 90% sequence identity to the polypeptide of SEQ ID NO: 3 of WO 2018/113743;
  (b) a polypeptide having at least 80% sequence identity to the polypeptide of SEQ ID NO: 6 of WO 2018/113743;
  (c) a polypeptide having at least 80% sequence identity to the polypeptide of SEQ ID NO: 9 of WO 2018/113743;
  (d) a polypeptide having at least 80% sequence identity to the polypeptide of SEQ ID NO: 12 of WO 2018/113743;
  (e) a polypeptide having at least 80% sequence identity to the polypeptide of SEQ ID NO: 15 of WO 2018/113743;
  (f) a polypeptide having at least 80% sequence identity to the polypeptide of SEQ ID NO: 18 of WO 2018/113743;
  (g) a polypeptide having at least 80% sequence identity to the polypeptide of SEQ ID NO: 21 of WO 2018/113743;
  (h) a polypeptide having at least 80% sequence identity to the polypeptide of SEQ ID NO: 24 of WO 2018/113743;
  (i) a polypeptide having at least 80% sequence identity to the polypeptide of SEQ ID NO: 27 of WO 2018/113743;
  (j) a polypeptide having at least 80% sequence identity to the polypeptide of SEQ ID NO: 30 of WO 2018/113743;
  (k) a polypeptide having at least 80% sequence identity to the polypeptide of SEQ ID NO: 33 of WO 2018/113743;
  (l) a polypeptide having at least 83% sequence identity to the polypeptide of SEQ ID NO: 38 of WO 2018/113743;

In one embodiment, the muramidase for use in the invention is an isolated polypeptide which is mentioned in WO 2018/113745 and is selected the group consisting of:
  (a) a polypeptide having at least 80% sequence identity to a polypeptide selected from the group consisting of SEQ ID NO: 3 of WO 2018/113745, SEQ ID NO: 9 of WO 2018/113745, SEQ ID NO: 12 of WO 2018/113745, SEQ ID NO: 15 of WO 2018/113745, SEQ ID NO: 18 of WO 2018/113745, SEQ ID NO: 21 of WO 2018/113745, SEQ ID NO: 24 of WO 2018/113745, SEQ ID NO: 27 of WO 2018/113745, SEQ ID NO: 33 of WO 2018/113745, SEQ ID NO: 36 of WO 2018/113745, SEQ ID NO: 42 of WO 2018/113745, SEQ ID NO: 45 of WO 2018/113745, SEQ ID NO: 48 of WO 2018/113745, SEQ ID NO: 51 of WO 2018/113745, SEQ ID NO: 54 of WO 2018/113745, SEQ ID NO: 57 of WO 2018/113745, SEQ ID NO: 60 of WO 2018/113745, SEQ ID NO: 63 of WO 2018/113745, SEQ ID NO: 66 of WO 2018/113745, SEQ ID NO: 69 of WO 2018/113745, SEQ ID NO: 75 of WO 2018/113745, SEQ ID NO: 80 of WO 2018/113745, SEQ ID NO: 83 of WO 2018/113745, SEQ ID NO: 86 of WO 2018/113745, SEQ ID NO: 98 of WO 2018/113745, SEQ ID NO: 101 of WO 2018/113745, SEQ ID NO: 104 of WO 2018/113745, SEQ ID NO: 107 of WO 2018/113745, SEQ ID NO: 116 of WO 2018/113745, SEQ ID NO: 119 of WO 2018/113745, SEQ ID NO: 122 of WO 2018/113745, SEQ ID NO: 125 of WO 2018/113745, SEQ ID NO: 128 of WO 2018/113745, SEQ ID NO: 131 of WO 2018/113745, SEQ ID NO: 134 of WO 2018/113745, SEQ ID NO: 137 of WO 2018/113745, SEQ ID NO: 140 of WO 2018/113745, SEQ ID NO: 143 of WO 2018/113745, SEQ ID NO: 146 of WO 2018/113745, SEQ ID NO: 149 of WO 2018/113745, SEQ ID NO: 152 of WO 2018/113745, SEQ ID NO: 155 of WO 2018/113745, SEQ ID NO: 158 of WO 2018/113745, SEQ ID NO: 221 of WO 2018/113745, SEQ ID NO: 224 of WO 2018/113745, SEQ ID NO: 227 of WO 2018/113745, SEQ ID NO: 230 of WO 2018/113745 and SEQ ID NO: 233 of WO 2018/113745;
  (b) a polypeptide having at least 84% sequence identity to a polypeptide selected from the group consisting of SEQ ID NO: 6 of WO 2018/113745, SEQ ID NO: 30 of WO 2018/113745 and SEQ ID NO: 72 of WO 2018/113745
  (c) a polypeptide having at least 86% sequence identity to the polypeptide of SEQ ID NO: 89 of WO 2018/113745;
  (d) a polypeptide having at least 82% sequence identity to a polypeptide selected from the group consisting of SEQ ID NO: 92 of WO 2018/113745, SEQ ID NO: 95 of WO 2018/113745 and SEQ ID NO: 110 of WO 2018/113745; and (e) a polypeptide having at least 81% sequence identity to the polypeptide of SEQ ID NO: 113 of WO 2018/113745;

The present invention is particularly suited for thermo labile muramidases. The term "thermo labile" as applied in the context of certain muramidases refers to the melting temperature, $T_m$, as determined using Differential Scanning calorimetry (DSC) at a pH of 5.5. For a thermo labile muramidase, $T_m$, is less than 100° C. In particular embodiments, the $T_m$ is less than 90° C., such as less than 80° C., less than 70° C., even less than 60° C. The determination of $T_m$, by DSC is performed at various PH-values using a VP-DSC from MicroCal. Scans are performed at a constant scan rate of 1.5° C./min from 20-90° C. Before running the DSC, The muramidase is desalted using NAP-5 columns (Pharmacia) equilibrated in the appropriate buffers (e.g. 0.2 M glycine-HCl, pH 2.5 or 3.0; 0.1 M sodium acetate, pH 5.5; 0.1M Tris-HCl, pH 7.0). Data handling may be performed using the MicroCal Origin software. The DSC measurements are performed as described in WO 2003/66847 which is hereby incorporated by reference.

In a particular embodiment of the present invention the muramidase of the granules of the present invention is thermo labile.

In a particular embodiment of the present invention the muramidase of the granules of the pelletized feed composition is thermo labile.

In a particular embodiment of the present invention the muramidase of the granules to be used for pelletized feed compositions is thermo labile.

The Coating

The core of the particle is coated with an inner salt layer surrounding the core, an outer hydrophobic layer surrounding the inner salt layer and optionally one or more further coating layers.

The Inner Salt Layer

The inner salt layer, may in a particular embodiment of the present invention contribute between 20-99% w/w of the granule, such as between 20-70% w/w, 30-60% w/w, 40-60% w/w or 50-60% w/w of the granule. In one embodiment, the inner salt layer. In one embodiment the inner salt layer comprises at least 60% w/w, e.g. 65% w/w or 70% w/w salt, which may be at least 75% w/w, e.g. at least 80% w/w, at least 85% w/w, e.g. at least 90% w/w or at least 95% w/w, even at least 99% w/w salt.

In a particular embodiment of the present invention the amount of salt in the inner salt layer of the granule constitutes at least 40% w/w of the inner salt layer.

In a particular embodiment of the present invention the amount of salt in the inner salt layer of the granules in the feed composition, such as e.g. stem treated feed compositions, constitutes at least 40% w/w of the inner salt layer.

In a particular embodiment of the present invention the amount of salt in the inner salt layer of the granules to be used for feed compositions, such as e.g. stem treated feed compositions, constitutes at least 40% w/w of the inner salt layer.

In a further particular embodiment of the present invention the amount of salt in the inner salt layer of the granule constitutes at least 50% w/w of the inner salt layer.

In a further particular embodiment of the present invention the amount of salt in the inner salt layer of the granules in the feed composition, such as e.g. stem treated feed compositions, constitutes at least 50% w/w of the inner salt layer.

In a further particular embodiment of the present invention the amount of salt in the inner salt layer of the granules to be used for feed compositions, such as e.g. stem treated feed compositions, constitutes at least 50% w/w of the inner salt layer.

In a yet further particular embodiment of the present invention the amount of salt in the inner salt layer of the granule constitutes at least 60% w/w of the inner salt layer.

In a yet further particular embodiment of the present invention the amount of salt in the inner salt layer of the granules in the feed composition, such as e.g. stem treated feed compositions, constitutes at least 60% w/w of the inner salt layer.

In a yet further particular embodiment of the present invention the amount of salt in the inner salt layer of the granules to be used for feed compositions, such as e.g. stem treated feed compositions, constitutes at least 60% w/w of the inner salt layer.

To be able to provide acceptable protection, the inner salt layer preferably has a certain thickness. In a particular embodiment of the present invention the inner salt layer is at least 15 µm thick. In a more particular embodiment the thickness of the inner salt layer is at least 22 µm. In an even more particular embodiment the total thickness of the inner salt layer is at least 30 µm. In a most particular embodiment the total thickness of the inner salt layer is at least 37 µm. In a most particular embodiment the total thickness of the inner salt layer is at least 45 µm. In a most particular embodiment the total thickness of the inner salt layer is at least 52 µm. In a particular embodiment of the present invention the thickness of the inner salt layer is below 100 µm. In a more particular embodiment the thickness of the inner salt layer is below 60 µm. In an even more particular embodiment the total thickness of the inner salt layer is below 40 µm.

In a particular embodiment of the present invention the thickness of the inner salt layer of the granule of the present invention is at least 30 µm. In another particular embodiment of the present invention the thickness of the inner salt layer of the granule of the present invention is at least 37 µm. In yet another particular embodiment of the present invention the thickness of the inner salt layer of the granule of the present invention is at least 45 µm.

In a particular embodiment of the present invention the thickness of the inner salt layer of the granules to be used for feed composition, such as e.g. the steam treated pelletized feed composition, is at least 30 µm. In another particular embodiment of the present invention the thickness of the inner salt layer of the granules to be used for feed composition, such as e.g. the steam treated pelletized feed composition, is at least 37 µm. In yet another particular embodiment of the present invention the thickness of the inner salt layer of the granules to be used for feed composition, such as e.g. the steam treated pelletized feed composition, is at least 45 µm.

In a particular embodiment of the present invention the thickness of the inner salt layer of the granules to be used for feed compositions, such as e.g. the steam treated pelletized feed compositions, is at least 30 µm. In another particular embodiment of the present invention the thickness of the inner salt layer of the granules to be used for feed compositions, such as e.g. the steam treated pelletized feed compositions, is at least 37 µm. In yet another particular embodiment of the present invention the thickness of the inner salt layer of the granules to be used for feed compositions, such as e.g. the steam treated pelletized feed compositions, is at least 45 μm. In one embodiment the coated granule is a granule according to WO 01/25412, where the ratio between the diameter of the coated granule and the diameter of the core unit (abbreviated DG/DC) for this type of granules is at least 1.1, particularly at least 1.5, more particularly at least 2, more particularly at least 2.5, more particularly at least 3, most particularly at least 4. DG/DC is however particularly below about 100, particularly below about 50, more particularly below 25, and most particularly below 10. A particularly range for DG/DC is about 4 to about 6. Thus, for such granules the thickness of the inner salt layer should be at least 25 μm. A particular thickness is at least 50 μm such as at least 75 μm, at least 100 μm, at least 150 μm, at least 200 μm, at least 250 μm or particularly at least 300 μm. The thickness of this kind of inner salt layer is usually below 800 μm. A particular thickness is below 500 μm such as below 350 μm, below 300 μm, below 250 μm, below 200 μm, below 150 μm or particularly below 80 μm.

The inner salt layer should encapsulate the core unit by forming a substantially continuous layer, i.e. as an inner salt layer having few or no holes, so that the core unit it is encapsulating has few or no uncoated areas. The inner salt layer should in particular be homogenous in thickness.

The salt to be added is preferably in the form of a salt solution or a salt suspension wherein the fine particles is less than 5 μm, such as less than 1 μm.

In a particular embodiment of the present invention it is preferred to use a solution of salt as inner salt layer, but if the used salts have low solubility it can be preferable to use a suspension of salt instead of a solution, to be able to add more salt pr. litre liquid added to the granules. In a particular embodiment of the present invention the inner salt layer is prepared in accordance with the coating in WO 03/55967.

Referring to the salt in the inner salt layer it can either be one particular salt or a mixture of salts. The salt used may be an inorganic salt, e.g. salts of sulfate, sulfite, phosphate, phosphonate, nitrate, chloride or carbonate or salts of simple organic acids (less than 10 carbon atoms e.g. 6 or less carbon atoms) such as citrate, malonate or acetate. Examples of cations in these salts are alkali or earth alkali metal ions, although the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used. Specific examples include $NaH_2PO_4$, $Na_2HPO_4$, $Na_3PO_4$, $(NH_4)H_2PO_4$, $K_2HPO_4$, $KH_2PO_4$, $Na_2SO_4$, $K_2SO_4$, $KHSO_4$, $ZnSO_4$, $MgSO_4$, $CuSO_4$, $Mg(NO_3)_2$, $(NH_4)_2SO_4$, sodium borate, magnesium acetate and sodium citrate.

The salt may also be a hydrated salt, i.e. a crystalline salt hydrate with bound water(s) of crystallization, such as described in WO 99/32595. Examples of hydrated salts include magnesium sulfate heptahydrate ($MgSO_4(7H_2O)$), zinc sulfate heptahydrate ($ZnSO_4(7H_2O)$), sodium phosphate dibasic heptahydrate ($Na_2HPO_4(7H_2O)$), magnesium nitrate hexahydrate ($Mg(NO_3)_2(6H_2O)$), sodium borate decahydrate, sodium citrate dihydrate and magnesium acetate tetrahydrate.

In an embodiment of the present invention the inner salt layer does not comprise a hydrated salt. In a particular embodiment of the present invention the inner salt layer does not comprise a salt comprising more than four water molecules at 50° C.

In a particular embodiment of the present invention the Specific examples of suitable salts of the invention are NaCl ($CH_{20°\ C.}=76\%$), $Na_2CO_3$ ($CH_{20°\ C.}=92\%$), $NaNO_3$ ($CH_{20°\ C.}=73\%$), $Na_2HPO_4$ ($CH_{20°\ C.}=95\%$), $Na_3PO_4$ ($CH_{25°\ C.}=92\%$), $NH_4Cl$ ($CH_{20°\ C.}=79.5\%$), $(NH_4)_2HPO_4$ ($CH_{20°\ C.}=93.0\%$), $NH_4H_2PO_4$ ($CH_{20°\ C.}=93.1\%$), $(NH_4)_2SO_4$ ($CH_{20°\ C.}=81.1\%$), KCl ($CH_{20°\ C.}=85\%$), $K_2HPO_4$ ($CH_{20°\ C.}=92\%$), $KH_2PO_4$ ($CH_{20°\ C.}=96.5\%$), $KNO_3$ ($CH_{20°\ C.}=93.5\%$), $Na_2SO_4$ ($CH_{20°\ C.}=93\%$, $K_2SO_4$ ($CH_{20°\ C.}=98\%$), $KHSO_4$ ($CH_{20°\ C.}=86\%$), $MgSO_4$ ($CH_{20°\ C.}=90\%$), $ZnSO_4$ ($CH_{20°\ C.}=90\%$ and sodium citrate ($CH_{25°\ C.}=86\%$).

In a particular embodiment of the present invention the salt is selected from the group consisting of NaCl, $Na_2CO_3$, $NaNO_3$, $Na_2HPO_4$, $Na_3PO_4$, $NH_4Cl$, $(NH_4)_2HPO_4$, $NH_4H_2PO_4$, $(NH_4)_2SO_4$, KCl, $K_2HPO_4$, $KH_2PO_4$, $KNO_3$, $Na_2SO_4$, $K_2SO_4$, $KHSO_4$, $MgSO_4$, $ZnSO_4$, NaCl and sodium citrate or mixtures thereof. In a more particular embodiment of the present invention the salt is selected from the group consisting of NaCl, $Na_2CO_3$, $NaNO_3$, $Na_2HPO_4$, $Na_3PO_4$, $NH_4Cl$, $(NH_4)_2HPO_4$, $NH_4H_2PO_4$, $(NH_4)_2SO_4$, KCl, $K_2HPO_4$, $KH_2PO_4$, $KNO_3$, $Na_2SO_4$, $K_2SO_4$, $KHSO_4$, NaCl and sodium citrate or mixtures thereof.

In a particular embodiment of the present invention the salt comprised in the inner salt layer of the granule of the present invention is selected from the group consisting of NaCl, $Na_2CO_3$, $NaNO_3$, $Na_2HPO_4$, $Na_3PO_4$, $NH_4Cl$, $(NH_4)_2HPO_4$, $NH_4H_{12}PO_4$, $(NH_4)_2SO_4$, KCl, $K_2HPO_4$, $KH_2PO_4$, $KNO_3$, $Na_2SO_4$, $K_2SO_4$, $KHSO_4$, $MgSO_4$, $ZnSO_4$, NaCl and sodium citrate or mixtures thereof.

In a particular embodiment of the present invention the salt comprised in the inner salt layer of the granule of the steam treated pelletized feed composition is selected from the group of NaCl, $Na_2CO_3$, $NaNO_3$, $Na_2HPO_4$, $Na_3PO_4$, $NH_4Cl$, $(NH_4)_2HPO_4$, $NH_4H_2PO_4$, $(NH_4)_2SO_4$, KCl, $K_2HPO_4$, $KH_2PO_4$, $KNO_3$, $Na_2SO_4$, $K_2SO_4$, $KHSO_4$, $MgSO_4$, $ZnSO_4$, NaCl and sodium citrate or mixtures thereof.

In a particular embodiment of the present invention the salt comprised in the inner salt layer of the the granules to be used for steam treated pelletized feed compositions is selected from the group of NaCl, $Na_2CO_3$, $NaNO_3$, $Na_2HPO_4$, $Na_3PO_4$, $NH_4Cl$, $(NH_4)_2HPO_4$, $NH_4H_2PO_4$, $(NH_4)_2SO_4$, KCl, $K_2HPO_4$, $KH_2PO_4$, $KNO_3$, $Na_2SO_4$, $K_2SO_4$, $KHSO_4$, $MgSO_4$, $ZnSO_4$, NaCl and sodium citrate or mixtures thereof.

The Outer Hydrophobic Layer

The outer hydrophobic layer, may in a particular embodiment of the present invention contribute between 1-10% w/w of the granule, such as between 1-5% w/w, or between 2-3% w/w of the granule. In one embodiment, the outer hydrophobic layer contributes about 2% w/w of the granule. In another embodiment, the outer hydrophobic layer contributes about 3% w/w of the granule. In a particular embodiment of the present invention the amount of hydrophobic coating material in the outer hydrophobic layer of the granule constitutes at least 60% w/w of the outer hydrophobic layer.

In a particular embodiment of the present invention the amount of hydrophobic coating material in the outer hydrophobic layer of the granules in the feed composition, such as e.g. stem treated feed compositions, constitutes at least 60% w/w of the outer hydrophobic layer.

In a particular embodiment of the present invention the amount of hydrophobic coating material in the outer hydrophobic layer of the granules to be used for feed compositions, such as e.g. stem treated feed compositions, constitutes at least 60% w/w of the outer hydrophobic layer.

To be able to provide acceptable protection, the outer hydrophobic layer preferably has a certain thickness. In a particular embodiment of the present invention the outer hydrophobic layer is at least 1 µm thick. In a more particular embodiment the thickness of the outer hydrophobic layer is at least 1.5 µm. In an even more particular embodiment the total thickness of the outer hydrophobic layer is at least 2 µm. In a most particular embodiment the total thickness of the outer hydrophobic layer is at least 4 µm. In a most particular embodiment the total thickness of the outer hydrophobic layer is at least 7 µm. In a particular embodiment of the present invention the thickness of the outer hydrophobic layer is below 10 µm. In a more particular embodiment the thickness of the outer hydrophobic layer is below 7 µm. In an even more particular embodiment the total thickness of the outer hydrophobic layer is below 4 µm.

In a particular embodiment of the present invention the thickness of the outer hydrophobic layer of the granule of the present invention is at least 1.5 µm. In another particular embodiment of the present invention the thickness of the outer hydrophobic layer of the granule of the present invention is at least 2 µm.

In a particular embodiment of the present invention the thickness of the outer hydrophobic layer of the granules to be used for feed compositions, such as e.g. the steam treated pelletized feed composition, is at least 1.5 µm. In another particular embodiment of the present invention the thickness of the outer hydrophobic layer of the granules to be used for feed compositions, such as e.g. the steam treated pelletized feed composition, is at least 2 µm.

In a particular embodiment of the present invention the thickness of the outer hydrophobic layer of the granules to be used for feed compositions, such as e.g. steam treated pelletized feed compositions, is at least 1.5 µm. In another particular embodiment of the present invention the thickness of the outer hydrophobic layer of the granules to be used for feed compositions, such as e.g. steam treated pelletized feed compositions, is at least 2 µm.

The outer hydrophobic layer should encapsulate the inner salt layer by forming a substantially continuous layer, i.e. an outer hydrophobic layer having few or no holes, so that the inner salt layer it is encapsulating has few or no uncoated areas. The outer hydrophobic layer should in a preferred embodiment be homogenous in thickness.

Referring to the hydrophobic coating material in the outer hydrophobic layer it can either be one particular hydrophobic coating material or a mixture of hydrophobic coating materials.

The hydrophobic coating material may include oils and/or waxes, including, without limitations, hydrogenated vegetable oils such as hydrogenated castor oil, hydrogenated palm kernel oil, hydrogenated palm oil, hydrogenated cotton seeds, hydrogenated soy bean oil and/or hydrogenated rapeseed oil, a blend of hydrogenated and unhydrogenated vegetable oil, 12-hyroxystearic acid, microcrystalline wax such as Cerit HOT, and high-melting paraffin waxes such as Mekon White.

Further hydrophobic coating materials included in the invention are combinations with water immiscible liquids or low melting point hydrophobic solids that produce a mixture with a reduced melting point. These include waxes, C26 and higher, paraffin waxes, cholesterol, fatty alcohols, such as cetyl alcohol, mono-, di- and/or triglycerides of animal and vegetable origin such as hydrogenated ox tallow, hydrogenated fat, hydrogenated castor oil, fat derivatives such as fatty acids, soaps, esters, hydrophobic starches such as ethyl cellulose, lecithin. The waxes may be of natural origin, meaning they may be animal, vegetable or mineral. Animal waxes include, without limitation, beeswax, lanolin, shellac wax and Chinese insect wax. Vegetable wax includes, without limitation, carnauba, candelilla, bayberry and sugar cane waxes. Mineral waxes include, without limitation, fossil or earth waxes including ozokerite, ceresin and montan or petroleum waxes, including paraffin and microcrystalline waxes. Alternatively the waxes may be synthetic or mixtures of natural and synthetic waxes. For example, synthetic or mixtures of natural and synthetic waxes may include low molecular weight partially oxidized polyethylene, which may be preferentially co-melted with paraffin. The fatty derivatives may be either fatty acids, fatty acid amides, fatty alcohols, fatty esters or mixtures of these. The acid amide may be stearamide. Sterols or long chain sterol esters may also be such as cholesterol or ergosterol.

A preferred hydrophobic coating material is palm oil or hydrogenated palm oil.

The Feed Composition

The granule of the present invention is suitable for use in animal feed compositions. The granule is mixed with feed substances. The characteristics of the granule allows its use as a component of a composition which is well suited as an animal feed, which is steam treated and subsequently pelletized.

The term animal includes all animals. Examples of animals are non-ruminants, and ruminants, such as cows, sheep and horses. In a particular embodiment, the animal is a non-ruminant animal. Non-ruminant animals include monogastric animals, e.g. pigs or swine (including, but not limited to, piglets, growing pigs, and sows); poultry such as turkeys and chicken (including but not limited to broiler chickens, layers); young calves; and fish (including but not limited to salmon).

The term feed or feed composition means any compound, preparation, mixture, or composition The feed of the present invention may comprise vegetable proteins. The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w).

Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal.

In a particular embodiment, the vegetable protein source is material from one or more plants of the family Fabaceae, e.g. soybean, lupine, pea, or bean.

In another particular embodiment, the vegetable protein source is material from one or more plants of the family Chenopodiaceae, e.g. beet, sugar beet, spinach or quinoa.

Other examples of vegetable protein sources are rapeseed, and cabbage.

Soybean is a preferred vegetable protein source.

Other examples of vegetable protein sources are cereals such as barley, wheat, rye, oat, maize (corn), rice, and sorghum.

Suitable animal feed additives are enzyme inhibitors, fat-soluble vitamins, water soluble vitamins, trace minerals and macro minerals.

Further, optional, feed-additive ingredients are colouring agents, aroma compounds, stabilisers, antimicrobial peptides, and/or at least one other enzyme selected from amongst phytases EC 3.1.3.8 or 3.1.3.26; xylanases EC 3.2.1.8; galactanases EC 3.2.1.89; and/or beta-glucanases EC 3.2.1.4.

Examples of anti microbial peptides (AMP's) are CAP18, Leucocin A, Tritrpticin, Protegrin-1, Thanatin, Defensin, Ovispirin such as Novispirin (Robert Lehrer, 2000), and variants, or fragments thereof which retain antimicrobial activity.

Examples of anti fungal polypeptides (AFP's) are the *Aspergillus giganteus*, and *Aspergillus niger* peptides, as well as variants and fragments thereof which retain antifungal activity, as disclosed in WO 94/01459 and PCT/DK02/00289.

Usually fat- and water-soluble vitamins, as well as trace minerals form part of a so-called premix intended for addition to the feed, whereas macro minerals are usually separately added to the feed.

The following are non-exclusive lists of examples of these components:

Examples of fat-soluble vitamins are vitamin A, vitamin D3, vitamin E, and vitamin K, e.g. vitamin K3.

Examples of water-soluble vitamins are vitamin B12, biotin and choline, vitamin B1, vitamin B2, vitamin B6, niacin, folic acid and panthothenate, e.g. Ca-D-panthothenate.

Examples of trace minerals are manganese, zinc, iron, copper, iodine, selenium, and cobalt.

Examples of macro minerals are calcium, phosphorus and sodium.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-10% fish meal; and/or 0-20% whey.

Preparation

Preparation of the Granule Core

The core of the granule of the invention may comprise a muramidase in the form of concentrated dry matter. In one embodiment, the concentrated dry matter is prepared by spray drying.

Methods for preparing the core can be found in Handbook of Powder Technology; Particle size enlargement by C. E. Capes; Volume 1; 1980; Elsevier. Preparation methods include known feed and granule formulation technologies, i.e.:

a) Spray dried products, wherein a liquid muramidase-containing solution is atomized in a spray drying tower to form small droplets which during their way down the drying tower dry to form an muramidase-containing particulate material. Very small particles can be produced this way (Michael S. Showell (editor); *Powdered detergents*; Surfactant Science Series; 1998; vol. 71; page 140-142; Marcel Dekker).

b) Layered products, wherein the muramidase is coated as a layer around a pre-formed inert core particle, wherein an muramidase-containing solution is atomized, typically in a fluid bed apparatus wherein the pre-formed core particles are fluidized, and the muramidase-containing solution adheres to the core particles and dries up to leave a layer of dry muramidase on the surface of the core particle. Particles of a desired size can be obtained this way if a useful core particle of the desired size can be found. This type of product is described in e.g. WO 97/23606 c) Absorbed core particles, wherein rather than coating the muramidase as a layer around the core, the muramidase is absorbed onto and/or into the surface of the core. Such a process is described in WO 97/39116.

d) Extrusion or pelletized products, wherein an muramidase-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the muramidase paste, which is harmful to the muramidase. (Michael S. Showell (editor); *Powdered detergents*; Surfactant Science Series; 1998; vol. 71; page 140-142; Marcel Dekker)

e) Prilled products, wherein an active powder is suspended in molten wax and the suspension is sprayed, e.g. through a rotating disk atomiser, into a cooling chamber where the droplets quickly solidify (Michael S. Showell (editor); *Powdered detergents*; Surfactant Science Series; 1998; vol. 71; page 140-142; Marcel Dekker). The product obtained is one wherein the muramidase is uniformly distributed throughout an inert material instead of being concentrated on its surface. Also U.S. Pat. Nos. 4,016,040 and 4,713,245 are documents relating to this technique f) Mixer granulation products, wherein an active-containing liquid is added to a dry powder composition of conventional granulating components. The liquid and the powder in a suitable proportion are mixed and as the moisture of the liquid is absorbed in the dry powder, the components of the dry powder will start to adhere and agglomerate and particles will build up, forming granulates comprising the muramidase. Such a process is described in U.S. Pat. No. 4,106,991 (NOVO NORDISK) and related documents EP 170360 B1 (NOVO NORDISK), EP 304332 B1 (NOVO NORDISK), EP 304331 (NOVO NORDISK), WO 90/09440 (NOVO NORDISK) and WO 90/09428 (NOVO NORDISK). In a particular product of this process wherein various high-shear mixers can be used as granulators, granulates consisting of enzyme as muramidase, fillers and binders etc. are mixed with cellulose fibres to reinforce the particles to give the so-called T-granulate. Reinforced particles, being more robust, release less enzymatic dust.

g) Size reduction, wherein the cores are produced by milling or crushing of larger particles, pellets, tablets, briquettes etc. containing the active material. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons).

h) Fluid bed granulation. Fluid bed granulation involves suspending particulates in an air stream and spraying a liquid onto the fluidized particles via nozzles. Particles hit by spray droplets get wetted and become tacky. The tacky particles collide with other particles and adhere to them and form a granule.

i) The cores may be subjected to drying, such as in a fluid bed drier. Other known methods for drying granules in the feed or enzyme industry can be used by the skilled person. The drying preferably takes place at a product temperature of from 25 to 90° C. For some muramidases it is important the cores comprising the muramidase contain a low amount of water before coating with the salt. If water sensitive muramidases are coated with a salt before excessive water is removed, it will be trapped within the core and it may affect the activity of the muramidase negatively. After drying, the cores preferably contain 0.1-10% w/w water.

Preparation of the Inner Salt Layer

The inner salt layer may be applied onto the granule core comprising the muramidase by atomization onto the core granules in a fluid bed, the inner salt layer may further be applied in vacuum mixers, dragée type coaters (pan-drum coaters), equipment for coating of seeds, equipment comprising rotating bottoms (eks. Roto Glatt, CF granulators (Freund), torbed processors (Gauda) or in rotating fluid bed processors such as Omnitex (Nara).

After applying the salt layer the granule may optionally be dried. The drying of the salt coated granule can be achieved by any drying method available to the skilled person, such as spray-drying, freeze drying, vacuum drying, fluid bed drying, pan drum coating and microwave drying. Drying of the salt coated granule can also be combined with granulation methods which comprise e.g. the use of a fluid bed, a fluid bed spray dryer (FSD) or a Multi-stage dryer (MSD).

Preparation of the Hydrophobic Outer Layer

Conventional coatings and methods as known to the art may suitably be used, such as the coatings described in Danish PA 2002 00473, WO 89/08694, WO 89/08695, 270 608 B1 and/or WO 00/01793. Other examples of conventional coating materials may be found in U.S. Pat. No. 4,106,991, EP 170360, EP 304332, EP 304331, EP 458849, EP 458845, WO 97/39116, WO 92/12645A, WO 89/08695, WO 89/08694, WO 87/07292, WO 91/06638, WO 92/13030, WO 93/07260, WO 93/07263, WO 96/38527, WO 96/16151, WO 97/23606, WO 01/25412, WO 02/20746, WO 02/28369, U.S. Pat. Nos. 5,879,920, 5,324, 649, 4,689,297, 6,348,442, EP 206417, EP 193829, DE 4344215, DE 4322229 A, DE 263790, JP 61162185 A and/or JP 58179492.

The coating may be prepared by the same methods as mentioned above in the section "Preparation of the core" and "Preparation of the salt coating".

The granules obtained can be subjected to rounding off (e.g. spheronisation), such as in a Marumeriser™, or compaction.

The granules can be dried, such as in a fluid bed drier. Other known methods for drying granules in the feed or enzyme industry can be used by the skilled person. The drying preferably takes place at a product temperature of from 25 to 90° C.

Manufacturing of Feed Pellets

In the manufacturing of feed pellets it is preferred to involve steam treatment prior to pelleting, a process called conditioning. In the subsequent pelleting step the feed is forced through a die and the resulting strands are cut into suitable pellets of variable length. During this conditioning step the process temperature may rise to 60-100° C.

The feed mixture is prepared by mixing the granules comprising the muramidase with desired feed components. The mixture is led to a conditioner e.g. a cascade mixer with steam injection. The feed is in the conditioner heated up to a specified temperature, 60-100° C., e.g. 60° C., 70° C., 80° C., 90° C. or 100° C. by injecting steam, measured at the outlet of the conditioner. The residence time can be variable from seconds to minutes and even hours. Such as 5 seconds, 10 seconds, 15 seconds, 30 seconds, 1 minute, 2 minutes, 5 minutes, 10 minutes, 15 minutes, 30 minutes and 1 hour. In a particular embodiment of the present invention the temperature is 100° C. and the residence time is 60 seconds.

In a particular embodiment of the present invention the process temperature during steam treatment is at least 60° C. In a more particular embodiment of the present invention the process temperature during steam treatment is at least 70° C. In an even more particular embodiment of the present invention the process temperature during steam treatment is at least 80° C. In a most particular embodiment of the present invention the process temperature during steam treatment is at least 90° C.

From the conditioner the feed is led to a press e.g. a Simon Heesen press, and pressed to pellets with variable length e.g. 15 mm. After the press the pellets are placed in an air cooler and cooled for a specified time e.g. 15 minutes.

A particular embodiment of the present invention is a method for manufacturing a feed composition comprising the steps of:

i. mixing feed components with granules comprising a core, an inner salt layer and an outer hydrophobic layer wherein the core comprises an muramidase,
ii. steam treating said composition (i), and
iii. pelleting said composition (ii).

In an embodiment, the muramidase present in the core of the granules has retained at least 75% of the activity of the muramidase in the core of the granules after steam pelleting the feed at 85 degrees Celsius compared to the activity before steam pelleting. In a further embodiment, the muramidase present in the core of the granules has retained at least 75% of the activity of the muramidase in the core of the granules after steam pelleting at 90 degrees Celsius compared to the activity before steam pelleting. In a further embodiment, the muramidase present in the core of the granules has retained at least 75% of the activity of the muramidase in the core of the granules after steam pelleting at 95 degrees Celsius compared to the activity before steam pelleting. In a yet further embodiment, the muramidase present in the core of the granules has retained at least 80% of the activity of the muramidase in the core of the granules after steam pelleting at 85 degrees Celsius compared to the activity before steam pelleting. In a yet further embodiment, the muramidase present in the core of the granules has retained at least 80% of the activity of the muramidase in the core of the granules after steam pelleting at 90 degrees Celsius compared to the activity before steam pelleting. In a yet further embodiment, the muramidase present in the core of the granules has retained at least 80% of the activity of the muramidase in the core of the granules after steam pelleting at 95 degrees Celsius compared to the activity before steam pelleting. In a still further embodiment, the muramidase present in the core of the granules has retained at least 85% of the activity of the muramidase in the core of the granules after steam pelleting at 85 degrees Celsius compared to the activity before steam pelleting. In a still further embodiment, the muramidase present in the core of the granules has retained at least 85% of the activity of the muramidase in the core of the granules after steam pelleting at 90 degrees Celsius compared to the activity before steam pelleting. In a still further embodiment, the muramidase present in the core of the granules has retained at least 85% of the activity of the muramidase in the core of the granules after steam pelleting at 95 degrees Celsius compared to the activity before steam pelleting.

Preferred Aspects

The present invention is further described by the following examples which should not be construed as limiting the scope of the invention.

1. A pelletized feed composition comprising a granule comprising a core and a coating, wherein the core comprises a muramidase and the coating comprises an inner salt layer and an outer hydrophobic layer.

2. The feed composition according to aspect 1 which has been exposed to steam treatment.

3. The feed composition according to aspect 1 or 2, wherein the inner salt layer contributes between 20-70% w/w of the granule.

4. The feed composition according to aspect 3, wherein the inner salt layer contributes between 30-60% w/w of the granule, such as 40-60% w/w.

5. The feed composition according to aspect 4, wherein the inner salt layer contributes between 50-60% w/w of the granule.

6. The feed composition according to aspect 1 or 2, wherein the inner salt layer contributes about 40% w/w of the granule.

7. The feed composition according to aspect 1 or 2, wherein the inner salt layer contributes about 50% w/w of the granule.

8. The feed composition according to aspect 1 or 2, wherein the inner salt layer contributes about 60% w/w of the granule.

9. The feed composition according to any one of aspects 1 to 8, wherein the thickness of the inner salt layer is at least 15 μm.

10. The feed composition according to any one of aspects 1 to 8, wherein the thickness of the inner salt layer is at least 22 μm.

11. The feed composition according to any one of aspects 1 to 8, wherein the thickness of the inner salt layer is at least 30 μm.

12. The feed composition according to any one of aspects 1 to 8, wherein the thickness of the inner salt layer is at least 37 μm.

13. The feed composition according to any one of aspects 1 to 8, wherein the thickness of the inner salt layer is at least 45 μm.

14. The feed composition according to any one of aspects 1 to 8, wherein the thickness of the inner salt layer is at least 52 μm.

15. The feed composition according to any one of aspects 1 to 14, wherein the inner salt layer comprises one or more salts selected from the group consisting of: NaCl, $Na_2CO_3$, $NaNO_3$, $Na_2HPO_4$, $Na_3PO_4$, $NH_4Cl$, $(NH_4)_2HPO_4$, $NH_4H_2PO_4$, $(NH_4)_2SO_4$, KCl, $K_2HPO_4$, $KH_2PO_4$, $KNO_3$, $Na_2SO_4$, $K_2SO_4$, $KHSO_4$, $MgSO_4$, $ZnSO_4$, sodium citrate and mixtures thereof.

16. The feed composition according to any one of aspects 1 to 15, wherein the inner salt layer comprises $Na_2SO_4$, $K_2SO_4$, $MgSO_4$ or a mixture thereof.

17. The feed composition according to any one of aspects 1 to 16, wherein the inner salt layer comprises $Na_2SO_4$.

18. The feed composition according to any one of aspects 1 to 17, wherein the outer hydrophobic layer contributes between 1-10% w/w of the granule.

19. The feed composition according to any one of aspects 1 to 18, wherein the outer hydrophobic layer contributes between 1-5% w/w of the granule.

20. The feed composition according to aspect 19, wherein the outer hydrophobic layer contributes between 2-3% w/w of the granule.

21. The feed composition according to aspect 20, wherein the outer hydrophobic layer contributes about 2% w/w of the granule.

22. The feed composition according to aspect 20, wherein the outer hydrophobic layer contributes about 3% w/w of the granule.

23. The feed composition according to any one of aspects 1 to 22, wherein the thickness of the outer hydrophobic layer is at least 1 μm.

24. The feed composition according to any one of aspects 1 to 22, wherein the thickness of the outer hydrophobic layer is at least 1.5 μm.

25. The feed composition according to any one of aspects 1 to 22, wherein the thickness of the outer hydrophobic layer is at least 2 μm.

26. The feed composition according to any one of aspects 1 to 22, wherein the thickness of the outer hydrophobic layer is at least 4 μm.

27. The feed composition according to any one of aspects 1 to 22, wherein the thickness of the outer hydrophobic layer is at least 7 μm.

28. The feed composition according to any one of aspects 1 to 27, wherein the outer hydrophobic layer comprises one or more hydrophobic coating materials selected from the group consisting of: hydrogenated castor oil, hydrogenated palm kernel oil, hydrogenated palm oil, hydrogenated cotton seeds, hydrogenated soy bean oil, hydrogenated rapeseed oil, a blend of hydrogenated and unhydrogenated vegetable oil, 12-hyroxystearic acid, microcrystalline wax, high-melting paraffin waxes and mixtures thereof.

29. The feed composition according to any one of aspects 1 to 28, wherein the outer hydrophobic layer comprises hydrogenated palm oil.

30. The feed composition according to any one of aspects 1 to 29, wherein the granule further comprises a process aid.

31. The feed composition according to any one of aspects 1 to 30, wherein the process aid is provided as powdering.

32. The feed composition according to aspect 30 or 31, wherein the process aid is $CaCO_3$, talcum, and/or kaolin.

33. The feed composition according to any one of aspects 1 to 32, wherein the granules have a particle size which is between 50 μm-2000 μm.

34. The feed composition according to any one of aspects 1 to 33, wherein the granules have a particle size which is between 100 μm-1500 μm.

35. The feed composition according to any one of aspects 1 to 34, wherein the granules have a particle size which is below 1200 μm.

36. The feed composition according to any one of aspects 1 to 35, wherein the granules have a particle size which is more than 250 μm.

37. The feed composition according to any one of aspects 1 to 36, wherein the granules have a particle size which is between 250 μm-1200 μm.

38. The feed composition according to any one of aspects 1 to 37, wherein the granules have a particle size which is between 250 μm-900 μm.

39. The feed composition according to any one of aspects 1 to 37, wherein the granules have a particle size which is between 600 μm-1200 μm.

40. The feed composition according to any one of aspects 1 to 37, wherein the granules have a particle size which is between 600 μm-900 μm.

41. The feed composition according to any one of aspects 1 to 37, wherein the granules have a mean particle size which is between 500 μm-700 μm.

42. The feed composition according to any one of aspects 1 to 41, wherein the muramidase is a GH25 muramidase.

43. The feed composition according to any one of aspects 1 to 42, wherein the muramidase has ability to lyse bacterial cell walls.

44. The feed composition according to any one of aspects 1 to 43, wherein the muramidase has lysozyme activity against the peptidoglycans found in the cell walls of *Micrococcus lysodeikticus*.

45. The feed composition according to any one of aspects 1 to 44, wherein the muramidase has lysozyme activity against *Lactobacillus johnsonii*.

46. The feed composition according to any one of aspects 1 to 45, wherein the muramidase is an isolated polypeptide which is selected from the group consisting of:
(a) a polypeptide having at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2 or to the mature polypeptide of SEQ ID NO: 4;
(b) a polypeptide encoded by a polynucleotide having at least 80%, at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1 or to the mature polypeptide coding sequence of SEQ ID NO: 3;
(c) a polypeptide encoded by a polynucleotide that hybridizes under medium-high stringency conditions with the mature polypeptide coding sequence of SEQ ID NO: 1 or SEQ ID NO: 3, or the full-length complement thereof;
(d) a variant of the mature polypeptide of SEQ ID NO: 2 or SEQ ID NO: 4, comprising a substitution, deletion, and/or insertion at one or more (e.g., several) positions; and
(e) a fragment a fragment of the polypeptide of (a), (b), (c) or (d) that has lysozyme activity.

47. The feed composition according to any one of aspects 1 to 46, wherein the muramidase is thermo labile.

48. The feed composition according to any one of aspects 1 to 47, wherein the muramidase is selected among polypeptides comprising or consisting of the mature polypeptide of SEQ ID NO: 2 or SEQ ID NO: 4.

49. The feed composition according to any one of aspects 1 to 48, wherein the humidity of the mash composition is at least 11% before pelleting and conditioning.

50. The feed composition according to any one of aspects 1 to 49, wherein the humidity of the mash composition is between 11 and 15% before pelleting and conditioning.

51. The feed composition according to any one of aspects 1 to 50, wherein the humidity of the mash composition is between 12 and 14% before pelleting and conditioning.

52. The feed composition according to any one of aspects 1 to 50, wherein the humidity of the mash composition is about 11% before pelleting and conditioning.

53. The feed composition according to any one of aspects 1 to 50, wherein the humidity of the mash composition is about 12% before pelleting and conditioning.

54. The feed composition according to any one of aspects 1 to 50, wherein the humidity of the mash composition is about 13% before pelleting and conditioning.

55. The feed composition according to any one of aspects 1 to 50, wherein the humidity of the mash composition is about 14% before pelleting and conditioning.

56. The feed composition according to any one of aspects 1 to 50, wherein the humidity of the mash composition is about 15% before pelleting and conditioning.

57. The feed composition according to any one of aspects 1 to 56, wherein the core further comprises a salt.

58. The feed composition according to aspect 57, wherein the salt is a stabilisator.

59. The feed composition according to aspect 57 or 58, wherein the salt is selected from the group consisting of: $Na_2SO_4$, $MgSO_4$ and $ZnSO_4$.

60. The feed composition according to aspect 57 or 58, wherein the salt is $Na_2SO_4$.

61. The feed composition according to any one of aspects 1 to 60, wherein the retained activity of the muramidase present in the core of the granules after steam pelleting at 85 degrees Celsius is at least 75% of the activity of the muramidase in the core of the granules before steam pelleting.

62. The feed composition according to any one of aspects 1 to 60, wherein the retained activity of the muramidase present in the core of the granules after steam pelleting at 90 degrees Celsius is at least 75% of the activity of the muramidase in the core of the granules before steam pelleting.

63. The feed composition according to any one of aspects 1 to 60, wherein the retained activity of the muramidase present in the core of the granules after steam pelleting at 95 degrees Celsius is at least 75% of the activity of the muramidase in the core of the granules before steam pelleting.

64. The feed composition according to any one of aspects 1 to 60, wherein the retained activity of the muramidase present in the core of the granules after steam pelleting at 85 degrees Celsius is at least 80% of the activity of the muramidase in the core of the granules before steam pelleting.

65. The feed composition according to any one of aspects 1 to 60, wherein the retained activity of the muramidase present in the core of the granules after steam pelleting at 90 degrees Celsius is at least 80% of the activity of the muramidase in the core of the granules before steam pelleting.

66. The feed composition according to any one of aspects 1 to 60, wherein the retained activity of the muramidase present in the core of the granules after steam pelleting at 95 degrees Celsius is at least 80% of the activity of the muramidase in the core of the granules before steam pelleting.

67. The feed composition according to any one of aspects 1 to 60, wherein the retained activity of the muramidase present in the core of the granules after steam pelleting at 85 degrees Celsius is at least 85% of the activity of the muramidase in the core of the granules before steam pelleting.

68. The feed composition according to any one of aspects 1 to 60, wherein the retained activity of the muramidase present in the core of the granules after steam pelleting at 90 degrees Celsius is at least 85% of the activity of the muramidase in the core of the granules before steam pelleting.

69. The feed composition according to any one of aspects 1 to 60, wherein the retained activity of the muramidase present in the core of the granules after steam pelleting at 95 degrees Celsius is at least 85% of the activity of the muramidase in the core of the granules before steam pelleting.

70. The feed composition according to any one of aspects 1 to 69, wherein the core is a homogeneous blend of enzymes including one or more muramidases, an inert particle with muramidase and optionally further enzymes applied onto it, or a homogenous blend of enzymes including one or more muramidases and materials which act as binders which are coated with one or more muramidases.

71. The feed composition according to any one of aspects 1 to 70, wherein the granules only release a low amount of dust.

72. The feed composition according to any one of aspects 1 to 71, wherein the granules result in little or no total dust when measured by the Heubach Type 1 assay or the Elutriation assay as described in the definition of dust.

73. The feed composition according to any one of aspects 1 to 72, wherein the dust is below 1000 μg/g in Heubach Type 1 assay and/or below 1000 μg/g in Elutriation assay. In a further aspect, the dust is below 500 μg/g in Heubach Type 1 assay, below 250 μg/g in Heubach Type 1 assay, below 100 μg/g in Heubach Type 1 assay or below 50 μg/g in Heubach Type 1 assay. In a yet further aspect, the dust is below 500 μg/g in Elutriation assay, below 250 μg/g in Elutriation assay, below 100 μg/g in Elutriation assay or below 50 μg/g in Elutriation assay.

74. The feed composition according to any one of aspects 1 to 73, wherein the shelf life of the granules is retained.

75. A granule comprising a core and a coating, wherein the core comprises a muramidase and the coating comprises an inner salt layer and an outer hydrophobic layer.

76. A granule comprising a core and a coating, wherein the core comprises a muramidase and the coating comprises an inner salt layer and an outer hydrophobic layer, wherein the granule comprises at least 75% of muramidase with retained activity after steam pelleting compared to the activity before steam pelleting, and wherein the granule further comprises one or more of the following:
  v. the particle size of the granule is below 1200 μm,
  vi. the thickness of the inner inner salt layer is at least 15 μm,
  vii. the thickness of the outer hydrophobic coating is at least 1 μm, and
  viii. the muramidase is thermo labile.

77. The granule according to aspect 75 or 76 which has been exposed to steam treatment.

78. The granule according to any one of aspects 75 to 77, wherein the inner salt layer contributes between 20-70% w/w of the granule.

79. The granule according to aspect 78, wherein the inner salt layer contributes between 30-60% w/w of the granule, such as 40-60% w/w.

80. The granule according to any one of aspects 75 to 78, wherein the inner salt layer contributes between 50-60% w/w of the granule.

81. The granule according to any one of aspects 75 to 78, wherein the inner salt layer contributes about 40% w/w of the granule.

82. The granule according to any one of aspects 75 to 78, wherein the inner salt layer contributes about 50% w/w of the granule.

83. The granule according to any one of aspects 75 to 78, wherein the inner salt layer contributes about 60% w/w of the granule.

84. The granule according to any one of aspects 75 to 83, wherein the thickness of the inner salt layer is at least 15 μm.

85. The granule according to any one of aspects 75 to 83, wherein the thickness of the inner salt layer is at least 22 μm.

86. The granule according to any one of aspects 75 to 83, wherein the thickness of the inner salt layer is at least 30 μm.

87. The granule according to any one of aspects 75 to 83, wherein the thickness of the inner salt layer is at least 37 μm.

88. The granule according to any one of aspects 75 to 83, wherein the thickness of the inner salt layer is at least 45 μm.

89. The granule according to any one of aspects 75 to 83, wherein the thickness of the inner salt layer is at least 52 μm.

90. The granule according to any one of aspects 75 to 89, wherein the inner salt layer comprises one or more salts selected from the group consisting of: $NaCl$, $Na_2CO_3$, $NaNO_3$, $Na_2HPO_4$, $Na_3PO_4$, $NH_4Cl$, $(NH_4)_2HPO_4$, $NR_4H_2PO_4$, $(NH_4)_2SO_4$, $KCl$, $K_2HPO_4$, $KH_2PO_4$, $KNO_3$, $Na_2SO_4$, $K_2SO_4$, $KHSO_4$, $MgSO_4$, $ZnSO_4$, sodium citrate and mixtures thereof.

91. The granule according to any one of aspects 75 to 90, wherein the inner salt layer comprises $Na_2SO_4$, $K_2SO_4$, $MgSO_4$ or a mixture thereof.

92. The granule according to any one of aspects 75 to 91, wherein the inner salt layer comprises $Na_2S_{0.4}$.

93. The granule according to any one of aspects 75 to 92, wherein the outer hydrophobic layer contributes between 1-10% w/w of the granule.

94. The granule according to any one of aspects 75 to 93, wherein the outer hydrophobic layer contributes between 1-5% w/w of the granule.

95. The granule according to any one of aspects 75 to 94, wherein the outer hydrophobic layer contributes between 2-3% w/w of the granuler.

96. The granule according to aspect 95, wherein the outer hydrophobic layer contributes about 2% w/w of the granule.

97. The granule according to aspect 95, wherein the outer hydrophobic layer contributes about 3% w/w of the granule.

98. The granule according to any one of aspects 75 to 97, wherein the thickness of the outer hydrophobic layer is at least 1 μm.

99. The granule according to any one of aspects 75 to 97, wherein the thickness of the outer hydrophobic layer is at least 1.5 μm.

100. The granule according to any one of aspects 75 to 97, wherein the thickness of the outer hydrophobic layer is at least 2 μm.

101. The granule according to any one of aspects 75 to 97, wherein the thickness of the outer hydrophobic layer is at least 4 μm.

102. The granule according to any one of aspects 75 to 97, wherein the thickness of the outer hydrophobic layer is at least 7 μm.

103. The granule according to any one of aspects 75 to 102, wherein the outer hydrophobic layer comprises one or more hydrophobic coating materials selected from the group consisting of: hydrogenated castor oil, hydrogenated palm kernel oil, hydrogenated palm oil, hydrogenated cotton seeds, hydrogenated soy bean oil, hydrogenated rapeseed oil, a blend of hydrogenated and unhydrogenated vegetable oil, 12-hyroxystearic acid, microcrystalline wax, high-melting paraffin waxes and mixtures thereof.

104. The granule according to any one of aspects 75 to 103, wherein the outer hydrophobic layer comprises hydrogenated palm oil.

105. The granule according to any one of aspects 75 to 104, wherein the granule further comprises a process aid.

106. The granule according to aspect 105, wherein the process aid is provided as powdering.

107. The granule according to aspect 105 or 106, wherein the process aid is $CaCO_3$, talcum, and/or kaolin.

108. The granule according to any one of aspects 75 to 107, wherein the granules have a particle size which is between 50 μm-2000 μm.

109. The granule according to any one of aspects 75 to 108, wherein the granules have a particle size which is between 100 μm-1500 μm.

110. The granule according to any one of aspects 75 to 109, wherein the granules have a particle size which is below 1200 μm.

111. The granule according to any one of aspects 75 to 110, wherein the granules have a particle size which is more than 250 μm.

112. The granule according to any one of aspects 75 to 111, wherein the granules have a particle size which is between 250 μm-1200 μm.

113. The granule according to any one of aspects 75 to 111, wherein the granules have a particle size which is between 250 μm-900 μm.

114. The granule according to any one of aspects 75 to 111, wherein the granules have a particle size which is between 600 μm-1200 μm.

115. The granule according to any one of aspects 75 to 111, wherein the granules have a particle size which is between 600 μm-900 μm.

116. The granule according to any one of aspects 75 to 111, wherein the granules have a mean particle size which is between 500 μm-700 μm.

117. The granule according to any one of aspects 75 to 116, wherein the muramidase is a GH25 muramidase.

118. The granule according to any one of aspects 75 to 117, wherein the muramidase has ability to lyse bacterial cell walls.

119. The granule according to any one of aspects 75 to 118, wherein the muramidase has lysozyme activity against the peptidoglycans found in the cell walls of *Micrococcus lysodeikticus*.

120. The granule according to any one of aspects 75 to 119, wherein the muramidase has lysozyme activity against *Lactobacillus johnsonii*.

121. The granule according to any one of aspects 75 to 120, wherein the muramidase is an isolated polypeptide which is selected from the group consisting of:
  (a) a polypeptide having at least 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 2 or to the mature polypeptide of SEQ ID NO: 4;
  (b) a polypeptide encoded by a polynucleotide having at least 80%, at least 85% at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 1 or to the mature polypeptide coding sequence of SEQ ID NO: 3;
  (c) a polypeptide encoded by a polynucleotide that hybridizes under medium-high stringency conditions with the mature polypeptide coding sequence of SEQ ID NO: 1 or SEQ ID NO: 3, or the full-length complement thereof;
  (d) a variant of the mature polypeptide of SEQ ID NO: 2 or SEQ ID NO: 4, comprising a substitution, deletion, and/or insertion at one or more (e.g., several) positions; and
  (e) a fragment a fragment of the polypeptide of (a), (b), (c) or (d) that has lysozyme activity.

122. The granule according to any one of aspects 75 to 121, wherein the muramidase is thermo labile.

123. The granule according to any one of aspects 75 to 122, wherein the muramidase is selected among polypeptides comprising or consisting of the mature polypeptide of SEQ ID NO: 2 or SEQ ID NO: 4.

124. The granule according to any one of aspects 75 to 123, wherein the humidity of the mash composition is at least 11% before pelleting and conditioning.

125. The granule according to any one of aspects 75 to 123, wherein the humidity of the mash composition is between 11 and 15% before pelleting and conditioning.

126. The granule according to any one of aspects 75 to 123, wherein the humidity of the mash composition is between 12 and 14% before pelleting and conditioning.

127. The granule according to any one of aspects 75 to 123, wherein the humidity of the mash composition is about 11% before pelleting and conditioning.

128. The granule according to any one of aspects 75 to 123, wherein the humidity of the mash composition is about 12% before pelleting and conditioning.

129. The granule according to any one of aspects 75 to 123, wherein the humidity of the mash composition is about 13% before pelleting and conditioning.

130. The granule according to any one of aspects 75 to 123, wherein the humidity of the mash composition is about 14% before pelleting and conditioning.

131. The granule according to any one of aspects 75 to 123, wherein the humidity of the mash composition is about 15% before pelleting and conditioning.

132. The granule according to any one of aspects 75 to 131, wherein the core further comprises a salt.

133. The granule according to aspect 132, wherein the salt is a stabilisator.

134. The granule according to aspect 132 or 133, wherein the salt is selected from the group consisting of: $Na_2SO_4$, $MgSO_4$ and $ZnSO_4$.

135. The granule according to aspect 132 or 133, wherein the salt is $Na_2SO_4$.

136. The granule according to any one of aspects 75 to 135, wherein the retained activity of the muramidase present in the core of the granules after steam pelleting at 85 degrees Celsius is at least 75% of the activity of the muramidase in the core of the granules before steam pelleting.

137. The granule according to any one of aspects 75 to 135, wherein the retained activity of the muramidase present in the core of the granules after steam pelleting at 90 degrees Celsius is at least 75% of the activity of the muramidase in the core of the granules before steam pelleting.

138. The granule according to any one of aspects 75 to 135, wherein the retained activity of the muramidase present in the core of the granules after steam pelleting at 95 degrees Celsius is at least 75% of the activity of the muramidase in the core of the granules before steam pelleting.

139. The granule according to any one of aspects 75 to 135, wherein the retained activity of the muramidase present in the core of the granules after steam pelleting at 85 degrees Celsius is at least 80% of the activity of the muramidase in the core of the granules before steam pelleting.

140. The granule according to any one of aspects 75 to 135, wherein the retained activity of the muramidase present in the core of the granules after steam pelleting at 90 degrees Celsius is at least 80% of the activity of the muramidase in the core of the granules before steam pelleting.

141. The granule according to any one of aspects 75 to 135, wherein the retained activity of the muramidase present in the core of the granules after steam pelleting at 95 degrees Celsius is at least 80% of the activity of the muramidase in the core of the granules before steam pelleting.

142. The granule according to any one of aspects 75 to 135, wherein the retained activity of the muramidase present in the core of the granules after steam pelleting at 85 degrees Celsius is at least 85% of the activity of the muramidase in the core of the granules before steam pelleting.

143. The granule according to any one of aspects 75 to 135, wherein the retained activity of the muramidase present in the core of the granules after steam pelleting at 90 degrees Celsius is at least 85% of the activity of the muramidase in the core of the granules before steam pelleting.

144. The granule according to any one of aspects 75 to 135, wherein the retained activity of the muramidase present in the core of the granules after steam pelleting at 95 degrees Celsius is at least 85% of the activity of the muramidase in the core of the granules before steam pelleting.

145. The granule according to any one of aspects 75 to 144, wherein the core is a homogeneous blend of enzymes including one or more muramidases, an inert particle with muramidase and optionally further enzymes applied onto it, or a homogenous blend of enzymes including one or more muramidases and materials which act as binders which are coated with one or more muramidases.

146. The granule according to any one of aspects 75 to 145, wherein the granules only release a low amount of dust.

147. The granule according to any one of aspects 75 to 146, wherein the granules result in little or no total dust when measured by the Heubach Type 1 assay or the Elutriation assay as described in the definition of dust.

148. The granule according to any one of aspects 75 to 147, wherein the dust is below 1000 μg/g in Heubach Type 1 assay and/or below 1000 μg/g in Elutriation assay. In a further aspect, the dust is below 500 μg/g in Heubach Type 1 assay, below 250 μg/g in Heubach Type 1 assay, below 100 μg/g in Heubach Type 1 assay or below 50 μg/g in Heubach Type 1 assay. In a yet further aspect, the dust is below 500 μg/g in Elutriation assay, below 250 μg/g in Elutriation assay, below 100 μg/g in Elutriation assay or below 50 μg/g in Elutriation assay.

149. The granule according to any one of aspects 75 to 148, wherein the shelf life of the granules is retained.

150. A method for feeding animals comprising administering the feed composition of any one of aspects 1 to 74 to an animal.

151. A method for manufacturing a feed composition comprising the steps of:
(i) mixing feed components with granules comprising a core, an inner coating and an outer coating wherein the core comprises a muramidase, the inner coating comprises a salt and the outer coating comprises a hydrophobic coating material,
(ii) steam treating said composition, and
(iii) pelleting said composition.

152. A method for improving the stability of muramidase comprising incorporating the muramidase in a feed composition according to any one of aspects 1 to 74 or a granule according to any one of aspects 75 to 149.

153. A method for improving the stability of muramidase in a mash composition having a humidity above 12% comprising incorporating the muramidase in a feed composition according to any one of aspects 1 to 74 or a granule according to any one of aspects 75 to 149.

154. The use of a granule comprising a core comprising a muramidase, an inner salt layer and an outer hydrophobic layer according to any one of aspects 75 to 149 for preparing steam treated pelletized feed compositions.

EXAMPLES

Example 1

Granule 1, granule comprising a core comprising a muramidase, and a salt layer on the core:
A powder mixture with the following composition

| |
|---|
| 960 g cellulose, Arbocel B0200 |
| 600 g dextrin, Kaolin |
| 2534 g spray dried GH25 Muramidase powder |
| 7552 g ground $Na_2SO_4$ | was granulated in a Lödige mixer FM 50 with a granulation fluid consisting of

| |
|---|
| 480 g Sucrose |
| 2220 g water |

The granulation was carried out as described in U.S. Pat. No. 4,106,991, example 1.

The granulate was dried in a fluid bed dryer to a water content of less than 1% and sifted to obtain a product with particle size between 250 and 1200 micrometers.

4.0 kg of above described granule cores were placed into a MP1 fluid bed.

The following mixture was prepared for applying a salt layer on the cores:
1600 g Na2SO4
4000 g water
The following bed set-up was used during coating:
Airflow: 215 m³/hour
Inlet temperature: 90° C.
Product temperature: 44° C.
Nozzle size: 1.2 mm
Nozzle pressure: 3.0 bar
After coating, the granules were dried for 10 min. to reach a temperature of 75° C. and finally cooled.

Granule 2, granule comprising a core comprising a muramidase, an inner salt layer on the core, and an outer hydrophobic layer on the inner salt layer.

2.0 kg of granule 1 was placed into a Lödige mixer L 5.
The following mixture was prepared for applying a hydrophobic layer on the salt layer:
40 g Melted hydrogenated palm oil
120 g Kaolin
After coating, the final product was cooled in an MP 2 fluid bed.

Measurements of Pelleting Stability

Granules 1 and 2 were pelletized using different pelleting conditions and different moisture content in feed formulation.

Experimental Set-Up

Approximately 85 g enzyme granulate was pre-mixed with 10 kg mash for 10 minutes in a small horizontal mixer. This premix was mixed with 190 kg mash for 10 minutes in a larger horizontal mixer. From the mixer the mash was led to the conditioner (a cascade mixer with steam injection) at a rate of approximately 300 kg/hour. The conditioner heated up the mash to 85° C., 90° C. and 95° C., respectively (measured at the outlet) by injecting steam. The residence time in the conditioner was also varied from 60 seconds to 120 seconds. From the conditioner the mash was led to a Simon Heesen press equipped with 3.0×35 mm horizontal die and pressed to pellets with a length of around 15 mm. After the press the pellets were placed in an air cooler and cooled for 15 minutes.

Mash formulation:

| | |
|---|---|
| 73.0 % | Grind corn |
| 21.5 % | Toasted soy grits |
| 4.0 % | Soy oil |
| 0.5 % | Vitamin/premix Farmix VLSVRK |

Water content of mash: 12% and 14%, respectively.

The activity of the ingoing enzyme granulates and the activities of the final pellets were analyzed and from these figures the residual activity was calculated.

Pelleting trial results with 12% moisture in mash:

| | | | % residual activity | |
|---|---|---|---|---|
| Formulation | Comprising | Coat | 90° C./ 60 sec | 90° C./ 120 sec |
| Product 1 | Granule 1 | 40% $Na_2SO_4$ layer | 75 | 71 |
| Product 2 | Granule 2 | 40% $Na_2SO_4$ inner layer + hydr. palm oil outer layer | 83 | 84 |

Pelleting trial results with 14% moisture in mash:

| | | | % residual activity | |
|---|---|---|---|---|
| Formulation | Comprising | Coat | 90° C./ 60 sec | 90° C./ 120 sec |
| Product 1 | Granule 1 | 40% $Na_2SO_4$ layer | 77 | 49 |
| Product 2 | Granule 2 | 40% $Na_2SO_4$ inner layer + hydr. palm oil outer layer | 83 | 68 |

Pelleting trial results with 14% moisture in mash and different temperatures:

| | | | % residual activity | | |
|---|---|---|---|---|---|
| Formulation | Comprising | Coat | 85° C./ 60 sec | 90° C./ 60 sec | 95° C./ 60 sec |
| Product 1 | Granule 1 | 40% $Na_2SO_4$ layer | 75 | 66 | 36 |
| Product 2 | Granule 2 | 40% $Na_2SO_4$ inner layer + hydr. palm oil outer layer | 89 | 77 | 49 |

From the results it is evident that the combination of an inner salt layer and an outer hydrophobic layer is improving pelleting stability significantly when the moisture content in the mash is increased compared to only a salt coating.

Example 2

Granule 3, granule comprising a core comprising a muramidase, and a salt layer on the core:

A powder mixture with the following composition

| | |
|---|---|
| 960 g | cellulose, Arbocel B0200 |
| 600 g | dextrin, Kaolin |
| 2534 g | spray dried GH25 Muramidase powder |
| 7552 g | ground $Na_2SO_4$ | was granulated in a Lödige mixer FM 50 with a granulation fluid consisting of

| | |
|---|---|
| 480 g | Sucrose |
| 2220 g | water |

The granulation was carried out as described in U.S. Pat. No. 4,106,991, example 1.

The granulate was dried in a fluid bed dryer to a water content of less than 1% and sifted to obtain a product with particle size between 250 and 1200 micrometers.

4.0 kg of above described granule cores were placed into a MP1 fluid bed.

The following mixture was prepared for applying a salt layer on the cores:

2000 g Na2SO4
5000 g water

The following bed set-up was used during coating:

Airflow: 215 m³/hour
Inlet temperature: 90° C.
Product temperature: 44° C.
Nozzle size: 1.2 mm
Nozzle pressure: 3.0 bar After coating, the granules were dried for 10 min. to reach a temperature of 75° C. and finally cooled.

Granule 4, granule comprising a core comprising a muramidase, an inner salt layer on the core, and an outer hydrophobic layer on the inner salt layer 2.0 kg of granule 3 was placed into a Lödige mixer L 5.

The following mixture was prepared for applying a hydrophobic layer on the salt layer:

40 g Melted hydrogenated palm oil
120 g Kaolin

After coating the final product was cooled in an MP 2 fluid bed.

Granule 5, granule comprising a core comprising a muramidase, an inner salt layer on the core, and an outer hydrophobic layer on the inner salt layer:

A powder mixture with the following composition

| |
|---|
| 960 g cellulose, Arbocel B0200 |
| 600 g dextrin, Kaolin |
| 2534 g spray dried GH25 Muramidase powder |
| 7552 g ground $Na_2SO_4$ | was granulated in a Lödige mixer FM 50 with a granulation fluid consisting of

| |
|---|
| 480 g Sucrose |
| 2220 g water |

The granulation was carried out as described in U.S. Pat. No. 4,106,991, example 1.

The granulate was dried in a fluid bed dryer to a water content of less than 1% and sifted to obtain a product with particle size between 250 and 1200 micrometers.

4.0 kg of above described granule cores were placed into a MP1 fluid bed.

The following mixture was prepared for applying a salt layer on the cores:

2400 g Na2SO4
6000 g water
The following bed set-up was used during coating:
Airflow: 215 m³/hour
Inlet temperature: 90° C.
Product temperature: 44° C.
Nozzle size: 1.2 mm
Nozzle pressure: 3.0 bar After coating, the granules were dried for 10 min. to reach a temperature of 75° C. and finally cooled.

Granule 6, granule comprising a core comprising a muramidase, an inner salt layer on the core, and an outer hydrophobic layer on the inner salt layer 2.0 kg of granule 5 were placed into a Lödige mixer L 5.
The following mixture was prepared for applying a hydrophobic layer on the salt layer:
40 g Melted hydrogenated palm oil
120 g Kaolin
After coating the final product was cooled in a MP 2 fluid bed.

Pelleting Stability

Product 1, 2, 3, 4 and 6 comprising granule 1, 2, 3, 4 and 6 respectively were pelletized using the conditions given in example 1 with increased water content in the mash of 14%.

| Formulation | Comprising | Coat | % residual activity 90° C./60 sec |
|---|---|---|---|
| Product 1 | Granule 1 | 40% $Na_2SO_4$ layer | 77 |
| Product 2 | Granule 2 | 40% $Na_2SO_4$ inner layer + hydr. palm oil outer layer | 83 |
| Product 3 | Granule 3 | 50% $Na_2SO_4$ layer | 76 |
| Product 4 | Granule 4 | 50% $Na_2SO_4$ inner layer + hydr. palm oil outer layer | 85 |
| Product 6 | Granule 6 | 60% $Na_2SO_4$ inner layer + hydr. palm oil outer layer | 94 |

Pelleting trial results with 14% moisture in mash and different temperatures:

| Formu-lation | Comprising | Coat | % residual activity | |
|---|---|---|---|---|
| | | | 90° C./ 60 sec | 95° C./ 60 sec |
| Product 3 | Granule 3 | 50 % $Na_2SO_4$ layer | 76 | 76 |
| Product 4 | Granule 4 | 50% $Na_2SO_4$ inner layer + hydr. palm oil outer layer | 85 | 79 |
| Product 6 | Granule 6 | 60% $Na_2SO_4$ inner layer + hydr. palm oil outer layer | 94 | 94 |

From the experiments it is clear that increased salt coating improves the pelleting stability significantly, and the stability is further increased with addition of an outer hydrophobic palm oil layer.

The invention claimed is:

1. A pelletized feed composition comprising a granule comprising a core and a coating, wherein the core comprises at least 15% w/w spray dried muramidase and wherein the coating comprises an inner salt layer and an outer hydrophobic layer.

2. The feed composition according to claim 1 which has been exposed to steam treatment.

3. The feed composition according to claim 1, wherein the inner salt layer contributes between 40-70% w/w of the granule.

4. The feed composition according to claim 1, wherein the inner salt layer comprises $Na_2SO_4$, $K_2SO_4$, $MgSO_4$ or a mixture thereof.

5. The feed composition according to claim 1, wherein the outer hydrophobic layer has a thickness of at least 1 μm.

6. The feed composition according to claim 1, wherein the outer hydrophobic layer comprises hydrogenated palm oil.

7. The feed composition according to claim 1, wherein the muramidase is a GH25 muramidase which has ability to lyse bacterial cell walls.

8. The feed composition according to claim 1, wherein said feed composition was formed from a mash composition having a humidity above 12%.

9. The feed composition according to claim 8, said mash composition having a humidity of about 13%.

10. The feed composition according to claim 8, said mash composition having a humidity of about 14%.

11. The feed composition according to claim 8, said mash composition having a humidity of about 15%.

12. The feed composition according to claim 1, wherein the retained activity of the muramidase present in the core of the granules after steam pelleting at 85 degrees Celsius is at least 75% of the activity of the muramidase in the core of the granules before steam pelleting.

13. A method comprising incorporating a spray dried muramidase into a pelletized feed composition according to claim 1.

14. A method comprising administering the pelletized feed composition of claim 1 to an animal.

15. A granule comprising a core and a coating, wherein the core comprises at least 15% w/w spray dried muramidase and wherein the coating comprises an inner salt layer and an outer hydrophobic layer, said outer hydrophobic layer having a thickness of at least 1 μm.

16. The granule according to claim 15, wherein said muramidase is thermolabile and retains at least 75% of its activity after steam pelleting at 85 degrees Celsius, wherein the granule has a particle size below 1200 μm, wherein the inner salt layer has a thickness of at least 15 μm, and wherein the outer hydrophobic coating has a thickness of 1-10 μm.

17. A method comprising incorporating a spray dried muramidase into a granule according to claim 15.

18. A method for manufacturing a pelletized feed composition comprising the steps of:
(i) mixing feed components with a plurality of granules according to claim 15 to produce a mash composition;
(ii) steam treating said mash composition to produce a steam-treated mash composition having a humidity above 12%; and
iii) pelleting said steam-treated mash composition.

19. A method comprising administering the granule of claim 15 to an animal.

20. A method for manufacturing a pelletized feed composition comprising the steps of:
(i) mixing feed components with a plurality of granules comprising a core, an inner coating and an outer coating, wherein the core comprises at least 15% w/w spray dried muramidase, wherein the inner coating comprises a salt, and wherein the outer coating comprises a hydrophobic coating material, thereby producing a mash composition;
(ii) steam treating said mash composition to produce a steam-treated mash composition having a humidity above 12%; and
(iii) pelleting said steam-treated mash composition.

* * * * *